US011583606B2

(12) United States Patent
Huang et al.

(10) Patent No.: US 11,583,606 B2
(45) Date of Patent: Feb. 21, 2023

(54) UV-C LED DISINFECTING APPARATUSES, SYSTEMS, AND METHODS

(71) Applicant: A-one Technology, LTD, Zhuhai (CN)

(72) Inventors: Yonglin Huang, Irvine, CA (US); Andy P. Huang, Irvine, CA (US); Liang Wang, Irvine, CA (US); Yongxing Huang, Zhuhai (CN); Xiangdong Shi, Zhuhai (CN)

( * ) Notice: Subject to any disclaimer, the term of this patent is extended or adjusted under 35 U.S.C. 154(b) by 310 days.

(21) Appl. No.: 16/947,682

(22) Filed: Aug. 12, 2020

(65) Prior Publication Data

US 2022/0016297 A1    Jan. 20, 2022

(51) Int. Cl.
| | | |
|---|---|---|
| *A61L 9/20* | (2006.01) | |
| *A41D 13/11* | (2006.01) | |
| *A61L 2/10* | (2006.01) | |
| *A61L 2/24* | (2006.01) | |

(52) U.S. Cl.
CPC ............ *A61L 9/20* (2013.01); *A41D 13/1138* (2013.01); *A41D 13/1161* (2013.01); *A61L 2/10* (2013.01); *A61L 2/24* (2013.01); *A61L 2202/11* (2013.01); *A61L 2202/121* (2013.01); *A61L 2202/122* (2013.01); *A61L 2202/14* (2013.01); *A61L 2209/111* (2013.01); *A61L 2209/12* (2013.01);
(Continued)

(58) Field of Classification Search
CPC ..... A61L 9/20; A61L 2/10; A61L 2/24; A61L 2202/11; A61L 2202/121; A61L 2202/122; A61L 2202/14; A61L 2209/111; A61L 2209/12; A61L 2209/14; A61L 2209/15; A41D 13/1138; A41D 13/1161; A41D 13/11
See application file for complete search history.

(56) References Cited

U.S. PATENT DOCUMENTS

| | | |
|---|---|---|
| 8,696,985 B2 | 4/2014 | Gil et al. |
| 9,522,201 B2 | 12/2016 | Sunkara et al. |
| 9,675,720 B2 | 6/2017 | Romo et al. |

(Continued)

OTHER PUBLICATIONS

Manuela Buonanno, David Welch, Igor Shuryak & David J. Brenner, Far-UVC light (222 nm) efficiently and safely inactivates airborne human coronaviruses, Scientific Reports, Jun. 24, 2020, Springer Nature, United States.

*Primary Examiner* — Regina M Yoo
(74) *Attorney, Agent, or Firm* — Cionca IP Law P.C.; Marin Cionca

(57) ABSTRACT

An ultraviolet (UV) germicidal irradiation system comprising: a light emitting diode (LED) disinfecting face mask comprising: a flexible mask body having a front surface and a back surface; a flexible printed circuitry (FPC) sheet disposed within the flexible mask body, the FPC sheet having a plurality of LEDs adapted to emit UV light, the plurality of LEDs facing the front surface; a vibration sensor electrically connected to the FPC sheet, the vibration sensor being adapted to detect vibrations; a UV-reflective layer disposed behind the FPC sheet, the UV-reflective layer being adapted to reflect the UV light; and a light diffusion layer disposed in front of the FPC sheet, the light diffusion layer being adapted to scatter the UV light; and a control module comprising: a central processing unit (CPU), an LED driver, and a power source; the CPU being in electrical communication with the LED driver and the vibration sensor.

7 Claims, 6 Drawing Sheets

(52) U.S. Cl.
CPC ....... *A61L 2209/14* (2013.01); *A61L 2209/15* (2013.01)

(56) References Cited

U.S. PATENT DOCUMENTS

| | | |
|---|---|---|
| 10,166,309 B2 | 1/2019 | Liao et al. |
| 2008/0265179 A1 | 10/2008 | Havens et al. |
| 2010/0132715 A1* | 6/2010 | Litz .......................... A62B 7/10 128/207.12 |
| 2018/0078798 A1* | 3/2018 | Fabian ................. A61B 5/0816 |
| 2018/0117194 A1 | 5/2018 | Dobrinsky et al. |
| 2019/0328916 A1 | 10/2019 | Koponen et al. |
| 2021/0345707 A1* | 11/2021 | Tleibi .................. A62B 18/025 |

* cited by examiner

UV-C LED DISINFECTING APPARATUSES, SYSTEMS, AND METHODS

CROSS-REFERENCE TO RELATED APPLICATIONS

This application claims the benefit of Chinese Application No. 202010686567.4, filed Jul. 16, 2020, which is hereby incorporated by reference, to the extent that it is not conflicting with the present application.

BACKGROUND OF INVENTION

1. Field of the Invention

The invention relates generally to electronic systems and devices utilizing ultraviolet (UV) light-emitting diodes (LEDs) for UV germicidal irradiation, and specifically to wearable articles containing UV LED systems and apparatuses for UV germicidal irradiation.

2. Description of the Related Art

The safe sanitization and disinfection of objects has arguably never been as poignant an issue as seen today. Various viruses, bacteria and other pathogens that cause disease and illness enter the human body through mucosal membranes found in the nose, oral cavity, and lips. Such pathogens can travel through the air and live for minutes and even hours at a time on various hard surfaces, such as tabletops, countertops, benches, chairs, bus seats, hand railings, cellphones, etc., and can be transferred to such surfaces via an infected person's coughing, sneezing, or spitting, for example. Once a healthy person touches the contaminated surface, these viruses and pathogens can easily and effectively be transmitted to the person's body, since the virus or pathogen now lives on the person's hands. Most notably and most pressing, the novel coronavirus, also known as COVID-19 (or more accurately SARS-CoV-2), is one such easily transmittable virus. The novel coronavirus, a now raging global pandemic, has infected millions of people worldwide and has caused the death of over half a million people (as of July 2020).

Experts in the medical field have stated that consistent cleaning and disinfecting of one's hands, as well as the avoidance of touching one's face, is an effective defense against viruses like COVID-19. The consistent cleaning and disinfecting of hard surfaces, which may carry the virus, has proven to be another effective defense against potentially contracting COVID-19. One such method of disinfection is the use of ultraviolet (UV) light. For more than a century now, UV light, which consists of photons of wavelength 200-400 nm, has been known to be effective in killing bacteria and viruses. Currently, UV light is used in hospitals, for example, to sterilize the air, various hard surfaces, and various medical equipment and instruments. Such technology is also being utilized for public transportation disinfection, such as the sterilization of buses, for example.

While current technologies that utilize UV light may be effective at disinfecting potentially contaminated objects and surfaces, UV light radiation exposure may pose a threat to humans. The aforementioned technologies typically utilize UV-C light, which are UV light rays having wavelengths between 200-280 nm. UV-C light rays are known to be quite effective at destroying DNA, and more specifically RNA (Ribose Nucleic Acid) in the case of COVID-19, within the cell walls of bacteria and viruses, which have peak DNA absorption spectrums between 250-265 nm, for example. The damaging of the DNA prevents the organism from replicating and becoming infectious. UV lamps and fluorescent tubes utilized today usually emit UV light across a broad spectrum, which may or may not match with the wavelength DNA absorption spectrum of bacteria and viruses. This spectrum profile mismatch, both in the center wavelength and across the spectrum envelope profile, is a physical and fundamental block to efficient UV light disinfection. Furthermore, human exposure to UV light at these wavelengths can be dangerous. As an example, over exposure of the human skin to UV light radiation at these wavelengths is known to cause sunburn, and in worst cases, skin cancer. Additionally, UV lamps and fluorescent tubes used as described above, are often large and bulky and can therefore be unwieldy. Moreover, in many cases, these devices may not be optimized for efficiency, and thus generate excess local heat and consume higher levels of power. Thus, adapting an effective UV light system at such known wavelengths into articles (e.g., a face mask) that come into close contact with the human skin would be dangerous if used for disinfection, as described above. Furthermore, adapting a UV light system into smaller personal articles for household or personal use would be highly ineffective utilizing known UV lamps and fluorescent tubes for the reasons described above.

Therefore, there is a need to solve the problems described above by providing electronic UV light systems and apparatuses for personal use in effectively and safely neutralizing viruses, bacteria, and other pathogens.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect, an LED disinfecting system is provided for facilitating UV germicidal irradiation of an object. The LED disinfecting system may comprise a power supply, an LED light source module having an LED driver, and control circuitry adapted to control and time the LED driver, wherein the power supply supplies power to the control circuitry and the LED driver. Thus, an advantage is the improvement in power and thermal efficiencies, and therefore, a reduction in potential burning damage incurred. An additional advantage is the improvement in safety for the user due to the reduction in potential burning damage. Another advantage is the increase in use-life, and therefore the cost effectiveness, for the apparatus retrofitted with the disclosed UV-C LED system.

In another aspect, a UV-C germicidal irradiation system is provided for disinfecting of air, the UV-C germicidal irradiation system comprising an LED disinfecting face mask. The LED disinfecting face mask may comprise: a mask body, a pair of ear straps attached at opposite sides of the mask body; a plurality of UV-C LEDs mounted on an FPC light emitting sheet disposed within the mask body; a UV-reflective sheet disposed behind the FPC light emitting sheet, such that the UV-reflective sheet can reflect UV-C light emitted from the plurality of LEDs; and a light diffusion sheet disposed in front of the FPC light emitting sheet, such that the light diffusion sheet can scatter the UV-C light emitted from the plurality of LEDs. Thus, an advantage is that the LED face mask may be comfortably worn by and accommodate users of various backgrounds. Thus, an advantage is that the FPC may allow the LED disinfecting face mask to maintain its flexibility and comfortability while also performing UV germicidal irradiation via the UV-C LEDs. An additional advantage is that, because any leaked UV light is reflected rather than lost, and is therefore capable of facilitating UV germicidal irradiation, the overall UV light usage efficiency may be improved. Another advantage is that the user may not experience uncomfortable and/or excess amounts of heat when wearing the LED face mask, promoting safety and comfortability. An additional advantage is the implementation of a smart disinfection function for the safe, efficient, and effective automatic UV germicidal irradiation within the LED face mask.

In another aspect, a UV-C germicidal irradiation system is provided for disinfecting of air, the UV-C germicidal irradiation system comprising an LED disinfecting face mask and a control module. The LED disinfecting face mask may comprise: a flexible mask body, a pair of ear straps attached at opposite sides of the mask body; a plurality of UV-C LEDs mounted on an FPC light emitting sheet disposed within the mask body; a UV-reflective sheet disposed behind the FPC light emitting sheet, such that the UV-reflective sheet can reflect UV-C light emitted from the plurality of LEDs; a light diffusion sheet disposed in front of the FPC light emitting sheet, such that the light diffusion sheet can diffuse the UV-C light emitted from the plurality of LEDs; and a vibration sensor electrically connected to the FPC sheet, the vibration sensor being adapted to detect vibrations in the flexible mask body. The control module may comprise: a central processing unit (CPU); an LED driver adapted to activate and deactivate the plurality of LEDs; and a rechargeable battery adapted to supply power to the CPU and the LED driver; the CPU being in electrical communication with the LED driver and the vibration sensor; the CPU being adapted to generate a light emission cycle using detected vibrations data received from the vibration sensor and cause the LED driver to activate and deactivate the plurality of LEDs according to the generated light cycle. Thus, an advantage is that the LED face mask may be comfortably worn by and accommodate users of various backgrounds. Thus, an advantage is that the FPC may allow the LED disinfecting face mask to maintain its flexibility and comfortability while also performing UV germicidal irradiation via the UV-C LEDs. An additional advantage is that, because any leaked UV light is reflected rather than lost, and is therefore capable of facilitating UV germicidal irradiation, the overall UV light usage efficiency may be improved. Another advantage is that the user may not experience uncomfortable and/or excess amounts of heat when wearing the LED face mask, promoting safety and comfortability. An additional advantage is the implementation of a smart disinfection function for the safe, efficient, and effective automatic UV germicidal irradiation within the LED face mask.

In another aspect, a UV-C germicidal irradiation system is provided for disinfecting of air, the UV-C germicidal irradiation system comprising an LED disinfecting face mask and a control module. The LED disinfecting face mask may comprise: a conical mask body having a front end and a back end, a central tunnel disposed centrally within and extending a length of the conical mask body, and a pair of ear straps attached at opposite sides of the back end; a central airflow tap disposed centrally in the front end, the central airflow tap joining a first end of the central tunnel; a removable filter screen and an air leakage ring surrounding the removable filter screen disposed centrally in the back end, the removable filter screen joining a second end of the central tunnel; a flexible printed circuitry (FPC) sheet disposed within the conical mask body concentrically surrounding the central tunnel, the FPC sheet having a plurality of UV-C LEDs adapted to emit UV-C light; a UV-reflective layer disposed behind the FPC sheet, such that the UV-reflective sheet can reflect UV-C light emitted from the plurality of LEDs; a light diffusion layer disposed in front of the FPC sheet, such that the light diffusion layer can scatter the UV-C light emitted from the plurality of LEDs; and at least one vibration sensor electrically connected to the FPC sheet, the at least one vibration sensor being adapted to detect vibrations in the conical mask body. The control module may comprise: a central processing unit (CPU); an LED driver adapted to activate and deactivate the plurality of LEDs; and a rechargeable battery adapted to supply power to the CPU and the LED driver; the CPU being in electrical communication with the at least one vibration sensor and the LED driver. Thus, an advantage is that the conical LED face mask may allow a user ease of breathability when the face mask is worn. Another advantage is the prevention or minimization of the spread of infectious diseases when a user who may be infected with an infectious disease exhales, coughs, sneezes, or laughs. An additional advantage is the implementation of a smart disinfection function for the safe, efficient, and effective automatic UV germicidal irradiation within the LED face mask.

In another aspect, a UV-C germicidal irradiation system for disinfecting of at least one object is provided, the UV-C germicidal irradiation system comprising an LED disinfecting bag and a control module. The LED disinfecting bag may comprise: a stretchable bag body having a front surface and an rear surface, and an interior cavity disposed centrally within the stretchable bag body; a zipper disposed in the front surface, the zipper being adapted to open and close the LED disinfecting bag; an FPC sheet disposed within the stretchable bag body adjacent to the interior cavity, the FPC sheet having a plurality of UV-C LEDs adapted to face toward the interior cavity; a UV-reflective sheet disposed behind the FPC sheet, such that the UV-reflective sheet can reflect UV-C light emitted from the plurality of LEDs; a light diffusion layer disposed in front of the FPC light emitting sheet, such that the light diffusion layer can scatter the UV-C light throughout the interior cavity; and a safety switch electrically connected to the FPC sheet, the safety switch being adapted to detect when the LED disinfecting bag is closed. The control module may comprise: a central processing unit (CPU); an LED driver adapted to activate and deactivate the plurality of LEDs; and a rechargeable battery adapted to supply power to the central processing unit and the LED driver; the CPU being in electrical communication with the safety switch and the LED driver. Thus, an advantage is that the user may not experience uncomfortable and/or excess amounts of heat when holding/wearing the LED disinfecting bag, promoting safety and comfortability. Another advantage is that the safety and wellbeing of the user may be maintained due to the reduction in potential direct exposure to UV-C light rays. An additional advantage is the efficient and safe UV sterilization of various objects placed within the LED disinfecting bag. Another advantage is that the user need not manually control the UV light emission cycles, increasing the ease of usability of the LED disinfecting bag.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which.

DETAILED DESCRIPTION

Figure 1:
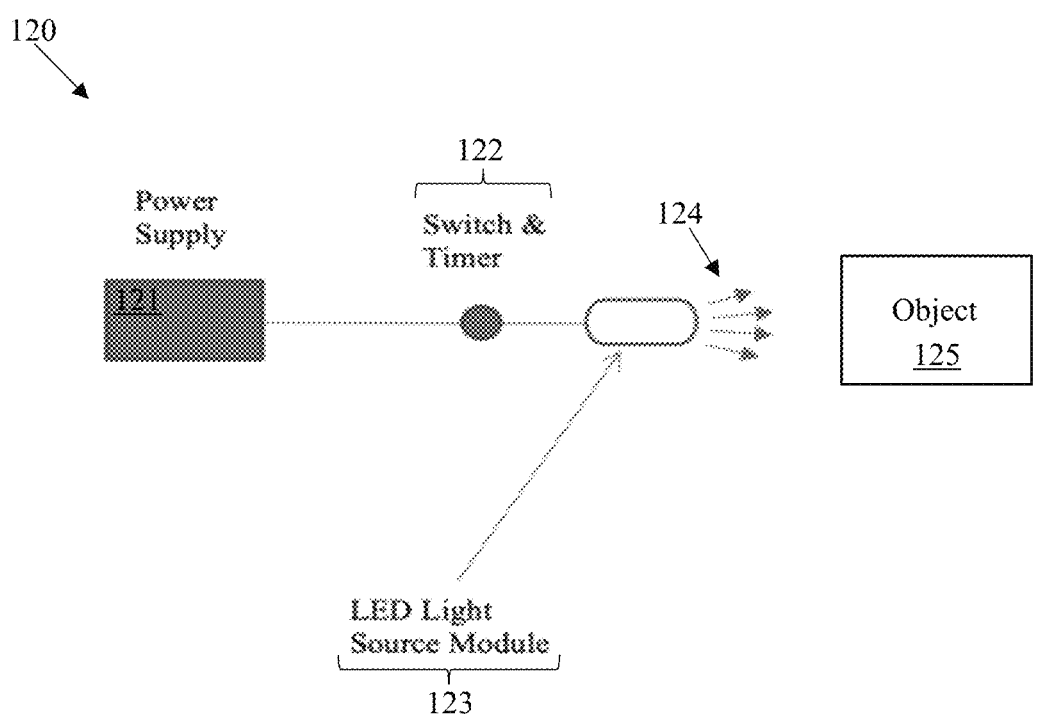
FIG. 1 is a block diagram illustrating a UV-C LED disinfecting system, according to an aspect.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the drawings and of the specification, some or all details about some structural components or steps that are known in the art are not shown or described if they are not necessary for the invention to be understood by one of ordinary skills in the art.

For the following description, it can be assumed that most correspondingly labeled elements across the figures (e.g., 210 and 310, etc.) possess the same characteristics and are subject to the same structure and function. If there is a difference between correspondingly labeled elements that is not pointed out, and this difference results in a non-corresponding structure or function of an element for a particular embodiment, example or aspect, then the conflicting description given for that particular embodiment, example or aspect shall govern.

"Logic" as used herein and throughout this disclosure, refers to any information having the form of instruction signals and/or data that may be applied to direct the operation of a processor. Logic may be formed from signals stored in a device memory. Software is one example of such logic. Logic may also be comprised by digital and/or analog hardware circuits, for example, hardware circuits comprising logical AND, OR, XOR, NAND, NOR, and other logical operations. Logic may be formed from combinations of software and hardware. On a network, logic may be programmed on a server, or a complex of servers. A particular logic unit is not limited to a single logical location on the network.

FIG. 1 is a block diagram illustrating a UV-C LED disinfecting system 120, according to an aspect. As shown as an example in FIG. 1, the UV-C LED disinfecting system ("UV-C LED disinfecting system," "LED disinfecting system," "LED system," "UV-C germicidal irradiation system") 120 may be implemented for the disinfection of various objects (represented by 125). As described in the Background above, ultraviolet (UV) light, particularly light along the UV-C spectrum (200-280 nm), may be emitted from a light source to effectively deactivate (damage the DNA of) infectious microorganisms like bacteria and viruses living on an object, for example. As described above, the light sources typically utilized for these applications are fluorescent tubes and lamps (e.g., mercury-based, or xenon-based), which can be quite large and bulky. Thus, implementing the UV-C disinfecting system 120 shown in FIG. 1 with fluorescent tubes or lamps would be very difficult for smaller, personal devices and apparatuses. Furthermore, even if the tubes or lamps were adapted to be small enough for a handheld apparatus, because of the high current draw needed to power such UV devices, the resultant UV-C light system would be far from optimized.

Thus, as shown in FIG. 1, the light source utilized for the systems and apparatuses disclosed herein is semiconductor light-emitting diodes (LEDs). As is known in the art, semiconductor LEDs are small in size, consume minimal power due to their very small current draw, and are easily adaptable and selectable for a wide number of light applications. LEDs are also very cost-effective, and because of the minimal current draw, may possess a much longer use-life than conventional lamps or tubes, which may burn out much sooner. Conventional semiconductor LEDs (those widely used in light applications) typically use gallium arsenide nitrite (GaN) as the semiconductor material. While such an LED is power efficient, as mentioned above, GaN-based LEDs emit light rays having wavelengths typically between 360 and 390 nm, which does not overlap well with the absorption spectrum of most pathogens, as described in the Background above. Semiconductor LEDs made of aluminum-doped gallium nitride (AlGaN), on the other hand, have light emission peaks around 270 nm; these wavelengths overlap well with the aforementioned pathogenic absorption spectrum (both in the center wavelength and the overall envelope profile). Thus, AlGaN-based LEDs would be much more effective at deactivating the cells of bacteria and viruses. Thus, the semiconductor LEDs 123 described herein below may preferably be AlGaN-based LEDs.

As shown in FIG. 1, the UV-C LED disinfecting system 120 may comprise a power supply 121. As an example, the power supply 121 may be a rechargeable battery, and may provide power to the system 120, as shown. The power supply 121 may connect to an external charger (e.g., power socket) for charging of the rechargeable battery, for example. It should be understood that the power supply 121 may be a replaceable off-the-shelf battery as well. The UV-C system 120 may further comprise a switch and timer ("switch and timer," "switch and timer circuitry," "timing circuitry," "control circuitry") 122, as shown. As will be described in greater detail later, the switch and timer 122 may be implemented on a central processing unit such as, for example, a microprocessor. The switch and timer 122 may electrically connect to the power supply 121 (via, e.g., electrical wires) for receiving electrical power, as an example. As an example, the control circuitry 122 may function as a timer which controls the duration that the LEDs operate and/or emit light (i.e., a light emission cycle). As shown, the timing circuitry 122 may connect electrically to the LED light source module ("LED light source module," "LED light source," "LEDs") 123. As an example, the control circuitry 122 may send an electrical control signal the LED light source module 123, such that the LED light source module 123 is caused to emit UV light. As will be described in detail later, the LED light source module 123 may be provided with an LED power and current regulating circuit (e.g., an LED driver) for supplying the LEDs with a constant current or a pulsed current, for example. The constant current may cause the LEDs to emit UV-C light for a preset amount of time (e.g., 30 seconds) and the pulsed current may cause the LEDs to emit UV-C light in pulses or flashes (e.g., in 0.1 second intervals), as an example. As an example, a commonly used LED driver has driving frequency capabilities ranging from a few 100 Hz to a few 100 kHz.

Conventionally, constant current (at approximately 100 mA) is used to drive an LED, depending on the application. However, using a pulsed current with an optimized duration ratio (e.g., 0.03 seconds on, 0.02 seconds off) may further help realize the electric current and power efficiency of the disclosed system. As an example, the LED modules 123 may comprise fluorescent materials for wavelength shifting or wavelength adjustment, so as to maintain the UV light emitted by the LEDs within the pathogenic DNA absorption spectrum. As an example, the fluorescent material helps maintain the stimulated UV-C radiation of each LED for a short period of time before decaying to zero. Thus, the driving current used to activate the LEDs 123 may be pulsed current since the fluorescent material will compensate for the brief duration between subsequent pulses, for example. Thus, less electric power may be used overall due to the improved optical wavelength spectrum efficiency of the UV-C LEDs 123 having the fluorescent materials. Additionally, providing a pulsed current to the LEDs 123 may reduce the amount of local heat that is generated, an excess of which could cause burning damage to the object under LED light exposure, or to the system 120 itself. Thus, an advantage is the improvement in power and thermal efficiencies, and therefore, a reduction in local heat generated and potential burning damage incurred. An additional advantage is the improvement in safety for the user due to the reduction in potential burning damage. Another advantage is the increase in use-life, and therefore the cost effectiveness, for the apparatus retrofitted with the disclosed LED system.

As shown in FIG. 1 and as described above, the LEDs 123 may, when directed by the switch and timer 122, emit UV-C light 124 directed onto the object 125 for UV germicidal irradiation. The object 125 may be any hard surface, handheld object, electrical device, or mediums like air, and even water, for example, that may contain pathogens. As an example, it may be advantageous to utilize a light source (placed at 123) that specifically emits far UV-C light. Far UV-C light, as is known, refers to UV light rays having wavelengths of about 222 nm. Recent scientific studies have shown that chronic irradiation with far UV-C light does not cause the formation of epidermal lesions on human skin, which are often associated with over exposure to traditional UV-C disinfection rays (at approximately 254 nm). Because far UV-C light rays share similar germicidal treatment capabilities with conventional UV-C light rays, while posing little to no harm to the human body, using a light source emitting far UV-C light may be preferred. Particularly, when adapting the LED system 120 shown in FIG. 1 in apparatuses that may operate in very close proximity to the human body, it may be preferable that mercury-free excimer lamps with quartz glass, that emit far UV-C light rays, are used, as an example. Alternatively, due to the semiconductor nature of LEDs, the material used to manufacture the LED may be modified to construct an LED capable of emitting far UV-C light rays, as an example. Thus, an advantage is the effective and optimized disinfection of objects while promoting safety for the user. As will be described in detail throughout this disclosure below, the LED system 120 shown in FIG. 1 may be adapted into a variety of exemplary apparatuses for the sterilization of various potentially virus-containing objects, as an example.

Figure 2:
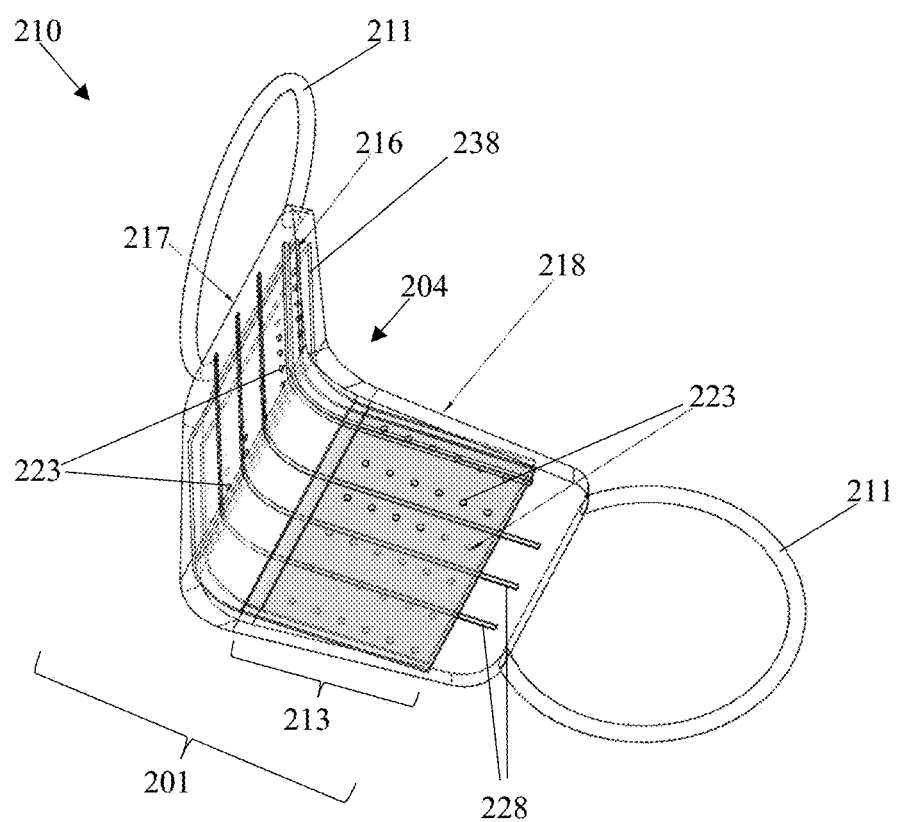
FIG. 2 illustrates a detailed perspective view of an example UV-C LED disinfecting face mask, according to an aspect.

FIG. 2 illustrates a detailed perspective view of an example UV-C LED disinfecting face mask 210, according to an aspect. As described previously when referring to FIG. 1, the UV-C LED system (120) may be adapted into a variety of apparatuses for facilitating UV germicidal irradiation. The UV-C LED system described above may be implemented into the UV-C LED disinfecting face mask ("UV-C LED disinfecting face mask," "LED disinfecting face mask," "LED face mask," "face mask") 210, which will be described in greater detail below.

As shown in FIG. 2, the LED face mask 210 may comprise a mask body 201 having a central fold line 204, as an example. As an example, the central fold line 204 may be flexible, such that the face mask 210 may fit comfortably and snugly around a user's face. Additionally, the face mask 210 may be folded along the central fold line 204, allowing the face mask 210 to be easily transportable and storable when not in use, as an example. As an example, the mask body 201 may be made from breathable and soft fabric or cloth (e.g., cotton). As shown in FIG. 2, the face mask 210 may further comprise a pair of ear straps ("ear straps," "ear loops," "fasteners") 211 attached at opposite ends of the face mask body 201. As an example, the pair of ear straps 211 may be made of a flexible and durable material such that the ear straps 211 fit snugly around the user's ears, causing the face mask 210 to further fit snugly around the user's face. Manufacturing the ear straps 211 of a flexible material may also enable the LED face mask 210 to universally fit on the faces of users of different ages, builds, facial structures, etc. Thus, an advantage is that the LED face mask may be comfortably worn by and accommodate users of various backgrounds. It should be understood that the LED face mask 210 may be adapted to be attached to the user's face by means other than the ear straps 211. As an example, the face mask body 201 may be provided with upper and lower straps that tie around the user's head and neck, respectively.

As shown, the LED face mask 210 may also be provided with an inner surface 218 and an outer surface 217, which, together, form the mask body 201, as an example. It should be understood that, when the LED face mask 210 is worn by the user, the inner surface 218 faces toward and contacts the user's face, and the outer surface 217 faces away from the user's face, as an example. As shown in FIG. 2, the LED face mask 210 may further comprise a plurality of UV-C LEDs 223, described previously when referring to FIG. 1, disposed within the mask body 201. As shown, the plurality of LEDs 223 may be arranged into rows and columns, such that UV-C light emitted from the plurality of LEDs 223 may be distributed more evenly across the outer surface 217 of the mask body 201, as an example. As shown as an example, each LED of the plurality of LEDs 223 may connect electrically (mounted onto) a light emitting sheet ("light emitting sheet," "luminescent sheet") 213 made of flexible printed circuitry (FPC), also called flex circuit wiring. The FPC light emitting sheet 213 (shaded in grey for clarity) may provide a flexible and lightweight electrical connection across the plurality of LEDs 223, while also occupying minimal physical space within the face mask body 201, as shown. As an example, the FPC may be constructed from polyethylene terephthalate (PET), which is naturally bendable plastic, having thin rolled annealed (RA) copper foil layers, which have high ductility and elongation, for the necessary electrical connections (connections to the LEDs 223, for example). The FPC thus allows electrical connections to be made while conforming to the shape of the attached surface (e.g., the face mask surface 218). Utilization of the FPC light emitting sheet 213 allows the plurality of LEDs 223 to be attached directly to the face mask fabric, providing a secure physical/mechanical connection between the electrical and nonelectrical portions of the face mask 210. Utilizing standard copper wires or traditional printed circuit boards, alternatively, would not provide the necessary structural integrity and flexibility needed for securely maintaining the LEDs within the soft and flexible face mask material. Thus, an advantage is that the FPC may allow the LED face mask to maintain its flexibility and comfortability while also performing UV germicidal irradiation via the UV-C LEDs. It should be understood that the FPC sheet 213 is provided as two halves, as shown, such that each half of the face mask body 201 comprises a plurality of LEDs 223, as shown.

As mentioned above, the mask body 201 may comprise the outer surface 217 and the inner surface 218, with the light emitting sheet 213 containing the plurality of LEDs 223 disposed between the outer surface 217 and the inner surface 218, as shown. As an example, the face mask 210 may also be provided with a protective UV light reflective plate or deposit film ("protective UV light reflective plate," "UV reflective plate," "protective plate") 238 positioned between the light emitting sheet 213 and the inner surface 218, as shown in FIG. 2. As shown, the plurality of LEDs 223 may be positioned on the FPC sheet 213 such that to face away from the user's mouth when the face mask 210 is worn. As such, UV radiation emitted by the plurality of LEDs 223 is directed away from the user, as an example, but it is still possible for UV radiation leakage to occur (UV radiation emitted toward the user). The protective plate 238 may thus comprise a highly reflective coating or material such that to reflect any leaked UV light outwardly away from the user's face, thus promoting safety for the user. Thus, an advantage is that the LED face mask may facilitate UV germicidal irradiation while protecting the user from exposure to potentially harmful UV radiation. An additional advantage is that, because any leaked UV light is reflected rather than lost, and is therefore capable of facilitating UV germicidal irradiation, the overall UV light usage efficiency may be improved. As an example, the UV reflective plate 238 may be made from any suitable material (e.g., silver, or other deposit metal film) to reflect away any excess UV-C light rays that may harm the user. Additionally, because the UV reflective plate or film is made of metallic material, the UV reflective plate or film may possess thermally conductive properties that more evenly distribute heat generated at local hotspots. Thus, another advantage is a more uniform thermal distribution that may provide thermal dissipation and insulation for the plurality of LEDs. It should be understood that the protective plate 238 may be constructed to be flexible or bendable, such that to maintain the flexibility of the LED face mask 210.

The protective plate 238, as an example, may also comprise an electrically insulating layer, in the form of a coating or film, for example, to provide insulation between the FPC sheet 213 and the inner surface 218. As an example, the electrically insulating coat may line the back surface of the protective plate 238, closest to the inner surface 218, such that to prevent and minimize any potential current flow or heat transfer from reaching the inner surface 218, and therefore, the user. Thus, an advantage is that the user may not experience uncomfortable and/or excess amounts of heat when wearing the LED face mask, promoting safety and comfortability. The electrically insulating layer may be chosen from a wide variety of readily available materials, such as acrylic coating, plastic coating, cellular glass, etc. As an example, for ease of construction of the protective plate 238, the protective plate 238 may be a sheet of insulating material coated with a highly reflective film/paint, such that the protective plate 238 is both UV reflecting and electrically insulating.

As shown in FIG. 2, the LED face mask 210 may further comprise a light diffusion plate ("light diffusion plate," "transparent diffusion plate," "diffusion plate") 216 disposed between the outer surface 217 and the FPC light emitting sheet 213, as an example. The light diffusion plate 216 may be positioned directly in front of the plurality of LEDs 223, as shown, such that to diffuse the UV-C light emitted by the plurality of LEDs 223, as an example. The transparent diffusion plate 216 may be made from a UV transparent acrylic material having a flat two-dimensional Fresnel structure. As an example, the two-dimensional Fresnel structure may cause the individual UV-C light rays to scatter, thus resulting in a more uniform spread of the UV-C light rays. The scattering of the UV-C light rays may thus enable all or nearly all portions of the outer surface 217 to be covered in UV-C radiation, thus facilitating germicidal irradiation across the entirety of the mask body 201. As an example, because of the even distribution of the UV-C light, the LED face mask 210 may efficiently disinfect the outer surface 217, while also using less UV light overall, and therefore less power, due to the diffusion and reflection (described above) within the mask body 201. Thus, because the UV-C light is spread uniformly throughout the LED face mask surface, an advantage is the improvement in overall UV light usage efficiency. As an example, the light diffusion plate 216 may also be provided with an electrically insulating coating or film, as similarly described above, to provide electrical and thermal insulation between the plurality of LEDs 223 and the outer surface 217.

It should be understood that the FPC light emission sheet 213, the UV-reflecting plate 238, and the light diffusion plate 216 may be configured within the mask body 201 to accommodate the user's breathing. As an example, the FPC sheet 213, the UV-reflecting plate 238, and the light diffusion plate 216 may be provided with a plurality of small (e.g., nano-sized) holes, such that air flow into and out of the LED face mask 210 is unrestricted.

As shown as an example, the LED face mask 210 may also be provided with a plurality of ribs 228 disposed horizontally across the outer surface 217 of the mask body 201. As an example, the plurality of ribs 228 may be three ribs, as shown. The plurality of ribs 228 may be made from semi-rigid structural material, such as plastic, for example, to protect the plurality of LEDs 223, the FPC light emission sheet 213, the UV reflective plate 238, and the light diffusion plate 216. As shown, the plurality of ribs 228 may be provided across the outer surface 217 to protect the aforementioned components (e.g., 223, 213) housed within the mask body 201 from damage that could be incurred from an accidental dropping of the LED face mask 210 on the ground, as an example. It should be understood, however, that because the FPC sheet 213, the UV-reflective plate 238, and the light diffusion plate 216 are already constructed of semi-rigid materials, the plurality of ribs 228 is not needed for protection.

As an example, the LED face mask 210 may also be provided with at least one vibration sensor (not shown), which will be described in greater detail when referring to FIG. 4. The at least one vibration sensor (labeled as Switch in FIG. 1, for example) may be built into the LED face mask 210 (electrically connected to the FPC sheet 213, for example), such that the sensor(s) are integral to the mask body 201, as an example. The at least one vibration sensor (along with the control circuitry, to be described later) may provide the LED face mask 210 with a smart disinfection function, for example. As will be described in more detail below, the at least one vibration sensor may detect the presence of a user, which thus provides a safety mechanism to prevent the plurality of LEDs 223 from emitting UV-C light rays accidentally or randomly, for example. The at least one vibration sensor may thus act as a switch that enables the plurality of LEDs 223 to operate only when the user is wearing the LED face mask 210. The LED face mask 210 may also be provided with a control box or module having a rechargeable battery, LED driver ("LED driver," "LED controller"), and control circuitry, which will be discussed later when referring to FIG. 4 below.

As mentioned throughout this disclosure above, the LED face mask 210 may be adapted for facilitating UV germicidal irradiation for preventing a user from contracting infectious diseases. As is quite commonplace currently, face masks are worn in public, such as outdoors, in retail centers, in restaurants, in schools, at grocery markets, etc., to prevent and limit the spread of infectious diseases, particularly COVID-19. Recently, scientific studies have suggested that COVID-19 can be transmitted through the air, necessitating the need for face masks that can effectively protect users from such airborne viruses. As described above, the LED face mask 210 shown in FIG. 2 is one such face mask. During use, and as the LED face mask 210 is worn by a user, the user may inhale and exhale air that may contain infectious microorganisms. These microorganisms, such as the coronavirus, may live on the face mask surface 217. The plurality of LEDs 223, emitting UV-C light rays that effectively destroy the DNA of these microorganisms, may disinfect the air before it is inhaled by the user, as well as after it is exhaled, for example. The plurality of LEDs 223 may also disinfect the outer surface 217 of the LED face mask 210, which may further potentially become contaminated through human touch (e.g., after the user puts the mask on or takes the mask off).

Figure 3:
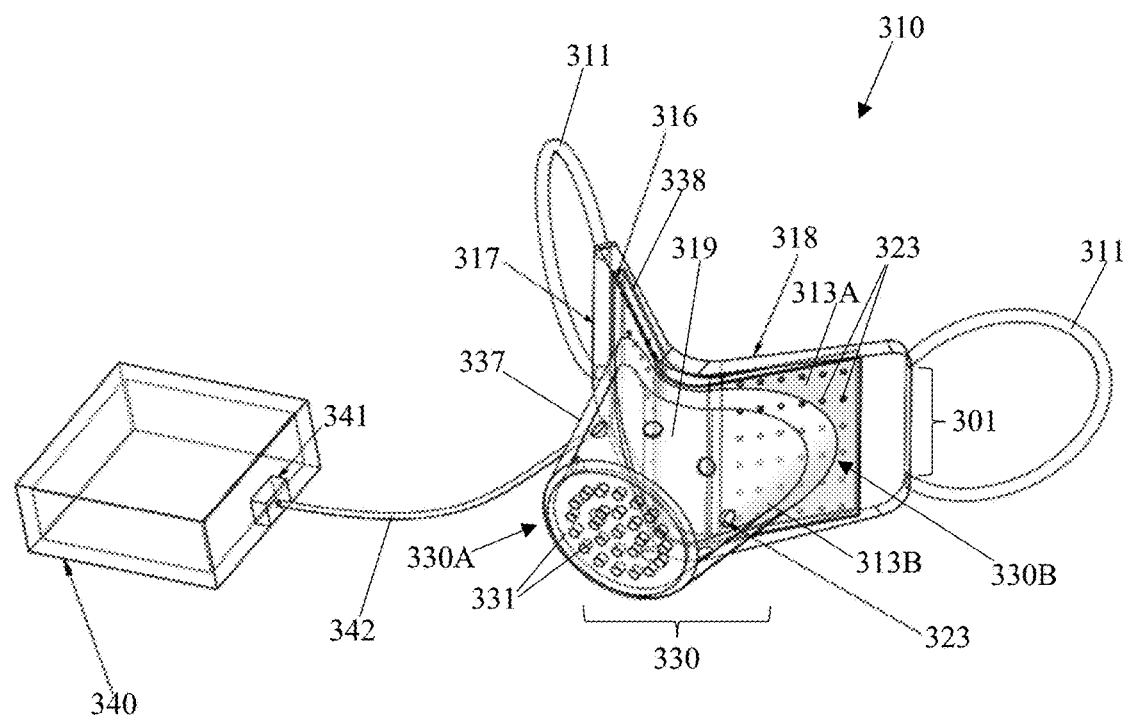
FIG. 3 illustrates a detailed perspective view of the example UV-C LED disinfecting face mask shown in FIG. 2, having a cone attachment and a connected control box, according to an aspect.
Figure 5:
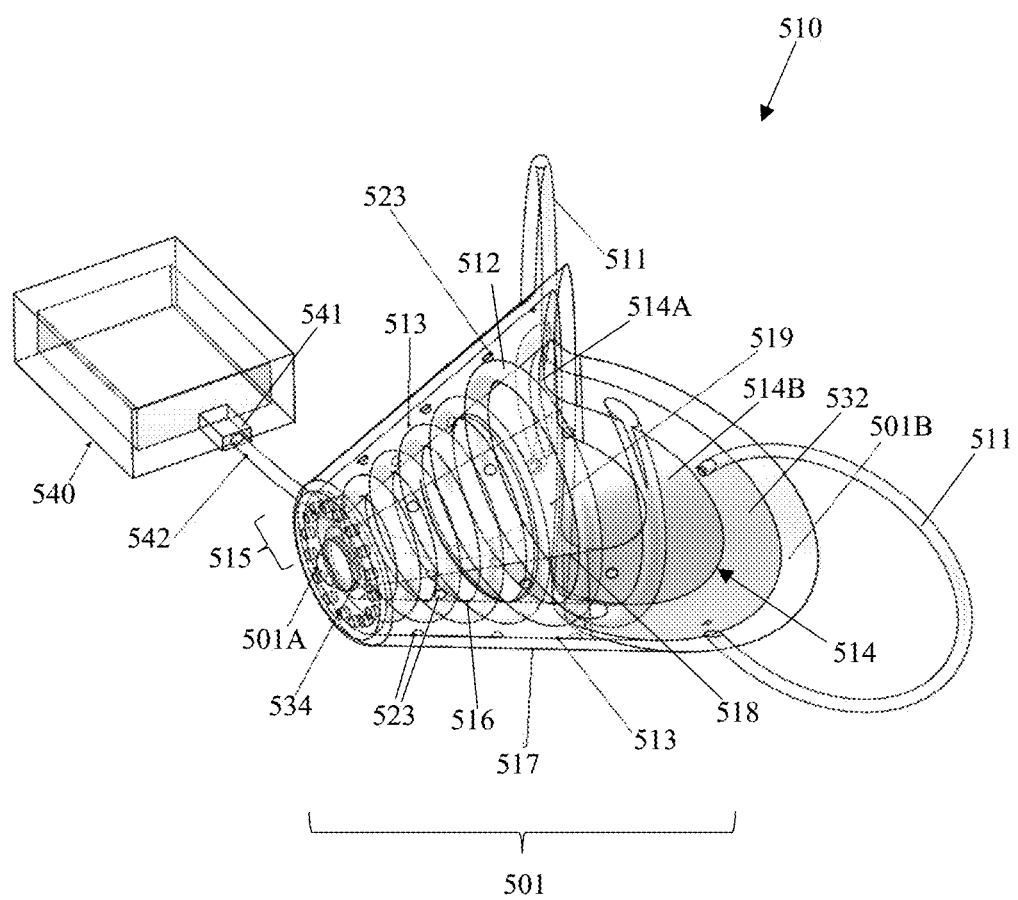
FIG. 5 illustrates a detailed perspective view of an example conical UV-C LED disinfecting face mask having a connected charging box, according to an aspect.

FIG. 3 illustrates a detailed perspective view of the example UV-C LED disinfecting face mask 210 shown in FIG. 2, having a cone attachment 330 and a connected control box 340, according to an aspect. As shown in FIG. 3, the LED face mask 310 described throughout this disclosure above may be provided with the cone attachment ("cone attachment," "cone portion," "LED cone") 330 for enhanced UV-C disinfection, which will be described herein below. The cone attachment 330 may alternatively be provided as a standalone face mask, an example of which is shown in FIG. 5. The LED face mask 310 may or may not comprise the same exemplary components described above when referring to FIG. 2, such as the pair of ear straps 311 attached to the mask body 301, the mask body 301 having an inner surface 318 and an outer surface 317. The LED face mask 310 may comprise the plurality of LEDs 323 electrically connected to the FPC light emitting sheet 313A, such that each half of the face mask body 301 contains LEDs 323, as shown. As described above, the LED face mask 310 may further comprise the reflective plate 338 disposed between the FPC sheet 313A and the inner surface 318, the reflective plate 338 having UV reflecting and electrically insulating properties. Furthermore, the LED face mask 310 may comprise the diffusion plate 316 disposed between the outer surface 317 and the FPC sheet 313A, as shown in FIG. 3, the diffusion plate 316 having light scattering and electrically insulating properties, as described above. Finally, the LED face mask 310 may be provided with vibration sensors (not shown) disposed within the mask body 301 that may provide input data for the control circuitry, which will be described in detail later.

As mentioned previously above, the cone attachment 330 may provide the LED face mask 310 with enhanced UV germicidal irradiation capabilities. The cone attachment 330 may be provided as a separate attachment or may be built into the face mask body 301, as an example. As shown in FIG. 3, the cone attachment 330 may be attached onto the mask body 301, such that a second end 330B of the cone attachment 330 abuts the mask outer surface 317. The joining of the cone attachment 330 and the mask body 301 thus creates a central airway/tunnel 319 within the cone attachment 330 for air to flow in and out of the LED face mask 310 during use. As an example, a first end 330A of the cone portion 330 may be provided with a plurality of airflow holes ("airflow holes," "air holes") 331, as shown. Thus, air may flow into the LED face mask 310 through the plurality of air holes 331, through the airway 319 and into the mask body 301. As shown, a first diameter of the first end 330A may be smaller than a second diameter of the second end 330B, such that the conical shape of the cone attachment 330 is created. The conical shape may, for example, due to a Venturi effect at the first end 330A, provide a more efficient airflow pattern resulting in higher volumetric airflow, making it easier for the user to breathe in air. Thus, air may flow unrestrictedly into and out of the cone portion due to the air holes and conical structure, as an advantage. Additionally, the cone portion 330 of the LED face mask 310 may be constructed of a durable material (e.g., plastic) to allow the LED face mask 310 to retain its conical structure during use.

As shown in FIG. 3, the cone portion 330 may comprise an outer surface 337 and an interior surface having an FPC light emission sheet 313B. As shown as an example, the FPC light emission sheet 313B may comprise a plurality of UV-C LEDs 323 disposed concentrically about the central airway 319, such that the air flowing through the cone may be disinfected by the plurality of LEDs 323 during use. As similarly described when referring to FIG. 2, the plurality of LEDs 323 within the cone attachment 330 may be electrically connected on the FPC sheet 313B, such that to adhere to the conical shape of the cone attachment, as an example.

It should be understood that the electronic components of the cone attachment 330 may connect electrically to the electronic components of the mask body 301 (via the FPC, for example), such that the plurality of LEDs 323 on both FPC sheets 313A, 313B of the LED face mask 310 may be simultaneously controlled. The FPC sheet 313B may also comprise a UV reflective layer (e.g., in the form of a coating or film) placed behind the plurality of LEDs 323 and within the outer surface 317. As discussed similarly above, the UV reflective layer (not shown) may line the "back" of the FPC light emission sheet 313B such that to reflect any leaked UV-C light rays that could potentially contact and harm the user's skin. Furthermore, as an example, the UV reflective layer may enable "recycling" of the already emitted UV-C light, such that the overall UV light usage efficiency of the LED face mask is increased, contributing to improved power efficiency, improved life expectancy of the apparatus, and improved safety for the user, as advantages.

As mentioned previously above, the LED face mask 310 may be provided with the control box ("control box," "control module") 340, as shown. As shown in FIG. 3, the control box 340 may be exterior to the face mask body 301, such that the two components are separate when not physically connected. As shown, the LED face mask 310 may further comprise a flexible cable 342. As an example, the flexible cable 342 may be electrically connected to the FPC light emitting sheets 313A, 313B that contain the plurality of LEDs 323, and may be attached to the mask body 301. The far end of the cable 342 may comprise an electrical connector 341 that may be inserted into the control box 340, as shown in FIG. 3. As mentioned above, the control box 340 may comprise a rechargeable battery (not shown), control circuitry (not shown), and an LED driver module (not shown), which will be discussed in detail when referring to FIG. 4. Thus, the control box 340 may provide power and operating instructions to the LED face mask 310 when the cable 342 is attached to the control box 340, as shown. It should be understood that in the embodiments shown in FIGS. 2 & 3, the LED face mask must be electrically connected to the control box 340 for the plurality of LEDs to operate. The control box 340 may also comprise a power chord (not shown) for attaching to an external socket for charging of the rechargeable battery, as an example. As shown, the control box 340 may be provided as a small and easily transportable attachment to the LED face mask 310. As an example, the control box 340 may fit into the user's pocket or in the user's bag or purse while the face mask 310 is in use. Thus, an advantage is the ease of transport, concealability, and use of the control box when attached to the LED face mask.

Figure 4:
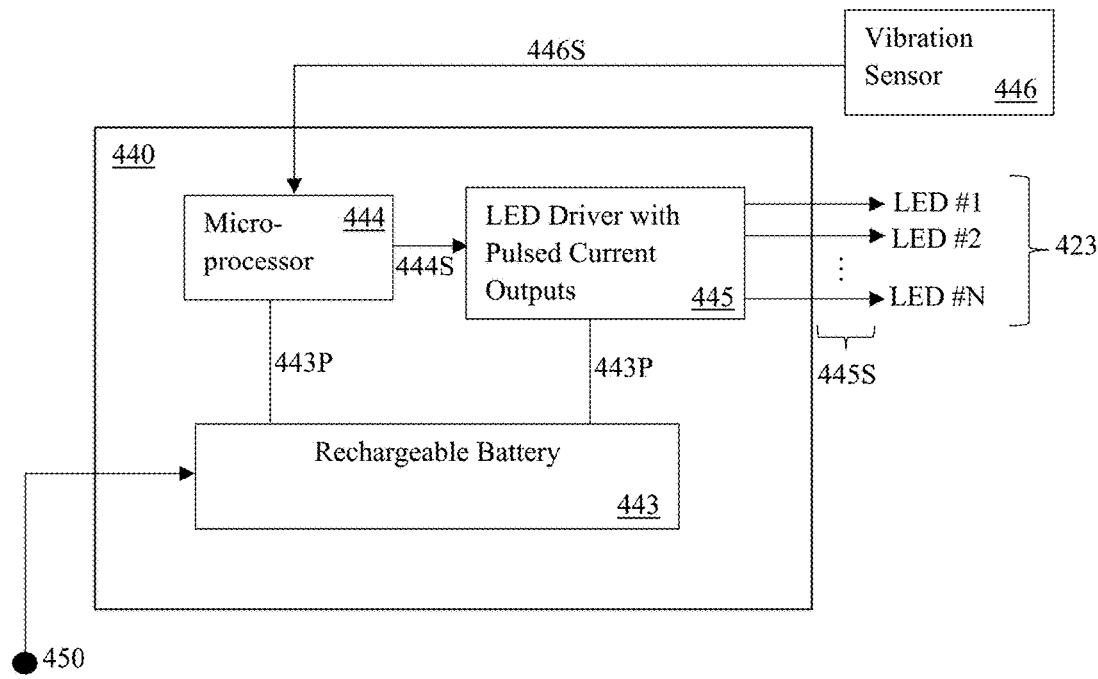
FIG. 4 is a block diagram illustrating the control module element shown in FIG. 3, according to an aspect.

FIG. 4 is a block diagram illustrating the control module element 340 shown in FIG. 3, according to an aspect. As described previously when referring to FIG. 3, the control box 440 may provide power and operating instructions for the plurality of UV-C LEDs of the LED face mask (e.g., 310). As shown in FIG. 4, the control box 440 may be provided with a microprocessor 444, which contains the control circuitry mentioned herein above, an LED driver 445, and a rechargeable battery 443. As should be understood, supporting electrical circuitry components (e.g., resistors, capacitors, voltage regulators, etc.) may also be provided in the control box 440 that are not shown for clarity.

As shown in FIG. 4, the rechargeable battery 443 may provide electric power to the microprocessor 444 and the LED driver 445 via power connections 443P, as an example. As should be understood, the rechargeable battery 443 indirectly provides power to the LED face mask disclosed herein above; the LED driver 445, which is powered by the rechargeable battery 443, supplies direct power to the plurality of LEDs of the face mask, which will be described in greater detail below. As shown, the rechargeable battery 443 may be charged via an external power source 450. The external power source 450 may be, for example, a 110-240 VAC outlet connector or a DC charger, or any other suitable charging means. The control box 440 may also be provided with a power switch (not shown) that, when actuated, causes the rechargeable battery 443 to supply power. It should be understood that the power switch (not shown) may alternatively be provided on the mask body (e.g., 301) of the LED face mask.

As shown in FIG. 4, the microprocessor 444 may draw power from the rechargeable battery 443, which may occur upon the actuation of the power switch (not shown), as mentioned above. As an example, the microprocessor 444 may be selected from any readily available microprocessor variety. It should be understood that the control circuitry may be implemented on any suitable central processing unit (CPU) as an alternative to the microprocessor, such as a micro programmable logic controller (PLC) chipset. The microprocessor 444 may be adapted to respond to input data with corresponding output data. The microprocessor 444 may thus control the operations of all the electrical components associated with the LED face mask directly or indirectly, as an example.

As described previously when referring to FIGS. 2 & 3, the LED face mask may comprise one or more vibration sensors 446, which may be disposed within the mask body and positioned close to the inner surface of the LED face mask, such that to be positioned close to the user's mouth when the mask is worn, as an example. When the user first puts on the LED face mask and begins to inhale and exhale, the vibration sensors 446 detect the presence of the user via vibrations on the inner mask surface (e.g., 218) caused by the user's breathing, as an example. The vibration sensors 446 may then transmit this vibration data via data signals 446S to the microprocessor 444, which may then interpret the data signals 446S. The vibration sensors 446 continuously transmit the vibration data signals 446S to the microprocessor 444, such that the microprocessor 444 can establish the user's breathing pattern (e.g., inhale, exhale, and cycle period). Once the user's breathing pattern has been identified, the microprocessor 444 may then transmit control data signals 444S to the LED Driver 445 for turning on and off the UV-C LEDs. As an example, the microprocessor 444 may, through the control data signals 444S, instruct the LED driver 445 to turn on and then off each LED of the plurality of LEDs according to a light emission cycle that corresponds to the breathing cycle of the user. Thus, the vibration sensors 446 are used to detect that the face mask is in place and to determine the user's breathing cycle, such that the UV-C LED operating cycle is assigned accordingly.

As mentioned above, the vibration sensors 446 may help establish a breathing pattern, in the form of vibration data 446S sent to the microprocessor 444. The microprocessor 444 may then generate an LED on and off cycle (i.e., light emission cycle), which is transmitted to the LED driver 445 via the control signal 444S, as shown. The LED driver 445 may then supply power to the plurality of LEDs 423 via pulsed current outputs 445S, as shown in FIG. 4. The pulsed current outputs 445S are a periodic/repeatable set of current pulses delivered at a set output value over user defined time intervals (i.e., a duration period). As described previously above, utilization of pulsed currents with a given duration ratio, compared with constant currents, may increase the power efficiency of the LEDs, therefore increasing the battery life of the rechargeable battery 443, as advantages. The improved power efficiency may also help reduce the local heat accumulation within the mask, since less current is flowing through the plurality of LEDs 423, as an example. The pulsed current outputs 445S may turn on the plurality of LEDs 423 for a period of time that matches or closely matches the length of time of the user's inhale and exhale. The pulsed current outputs 445S, sent by the LED driver 445 and controlled by the microprocessor 444, may also turn off the plurality of LEDs 423 for a period of time that matches or closely matches the length of time between the user's inhale and exhale (i.e., the pause), for example. Thus, the LED face mask may disinfect the air as it is both inhaled and exhaled by the user. Because the vibration sensors 446 continuously monitor the user's breathing pattern (as described above), a change in breathing pattern caused by a change in activity (e.g., running, talking) may be captured by the microprocessor 444, such that the LED driver 445 is instructed to update the pulsed current duration ratio to match/closely match the changed breathing pattern. Thus, an advantage is the implementation of a smart disinfection function for the safe, efficient, and effective automatic UV germicidal irradiation within the LED face mask.

As mentioned above, utilization of pulsed currents may increase the power efficiency of the plurality of LEDs, and therefore, the power efficiency of the LED disinfecting face mask as a whole. As an example, let driving current be a pulsed current having an on/off duration or duty cycle, of 50% (i.e., on 50% of the time and off 50% of the time). As is known, the power consumption of a common current device is equal to $I^2R$, where I is the current draw and R is the resistance. For simplicity, let the current value be 1 amp (A) and let the resistance be 1 ohm. At constant current, the resultant power is thus 1W. Now, let the current be pulsed current with the 50% on/off duration. The current is then overall an average equal to 0.5 A. Solving for the power, the result is 0.25 W. The actual power consumption of a pulsed drive current may thus be only 25%, or 75% lower than that, of the power consumption of a constant driving current, per this example.

As an example, the LED Driver 445 may be selected from any readily available LED driver variety that may be suitable to the current driving needs described above. As is known in the art, the LED Driver 445 may convert the higher voltage supplied by the rechargeable battery 443 to a low voltage and current source and may also maintain the current flow through the plurality of LEDs 423 at its rated level (e.g., 100 mA). It should be understood that the data signals 446S, 445S, for example, may all travel between the control box 340 and the LED face mask 310 via the cable 342 (using, for example, I2C communication protocol). It should also be understood that the sizes of the microprocessor 444, rechargeable battery 443, and LED driver 445 may be selected to be sufficiently small enough to fit within the control box 440 when assembled, for example, such that to enable the control box's 440 transportability and concealability. While the control module circuitry shown in FIG. 4 was described herein above as being implemented physically separate from the LED face mask, it should be understood that the control module circuitry may be, in whole or in part, implemented within the LED face mask itself, such that it is integral to the mask body, which will be described in another exemplary embodiment below.

FIG. 5 illustrates a detailed perspective view of an example conical UV-C LED disinfecting face mask 510 having a connected control box 540, according to an aspect.

FIG. 5 illustrates another exemplary embodiment of the LED face mask (e.g., 310) described herein above. As shown in FIG. 5, the conical UV-C LED disinfecting face mask ("conical UV-C LED disinfecting face mask," "conical LED disinfecting face mask," "conical LED face mask," "LED face mask") 510 may simplify the design of the LED face mask shown in FIG. 3, for example, such that the conical portion (e.g., 330) is implemented as completely integral to the face mask body (e.g., 301), as mentioned previously when referring to FIG. 3. As will be described throughout this disclosure below, the conical LED face mask 510 may be provided for the effective, efficient, and safe UV germicidal irradiation of infectious microorganisms traveling through the air.

As shown in FIG. 5, the conical LED face mask 510 may comprise a conical mask body 501, which may be provided with a pair of stretchable ear straps 511 attached at opposite sides of the mask body 501. As described similarly above, the mask body 501 may be provided with any alternate suitable fastening means (e.g., head and neck ties) for attaching the conical LED face mask 510 to the user's face, as an example. The ear straps 511 may also be adjustable such that the tightness of the pair of ear straps 511 may be changed as needed to achieve a comfortable seal between the user and the conical LED face mask 510. As an example, the mask body 501 may be constructed of a lightweight and durable material (e.g., plastic), such that the conical LED face mask 510 comfortably stays in place while worn. As shown, the mask body 501 may further comprise two opposite ends 501A, 501B. As shown as an example, the first end ("first end," "front end") 501A may have a first diameter smaller than a second diameter of the second end ("second end," "rear end") 501B, such that the conical shape of the mask body 501 is formed. As shown in FIG. 5, the second end 501B may be provided with a geometric structure closely resembling the natural curvature of the human face (e.g., nose and cheekbones). Thus, the conical LED face mask 510 may naturally and comfortably sit over the user's face during use. Thus, an advantage is that the user may experience continuous comfort for the complete duration of time that the conical LED face mask is worn.

As an example, the second end 501B of the mask body 501 may be provided with a filter screen ("filter screen," "screen net," "filter") 514, as shown. As shown in FIG. 5, the screen net 514 may comprise a generally circular shape and may be made of soft fabric material for ease of usability and comfort, as an example. As shown, the screen net 514 may further comprise two sides, an inner screen side 514A and an outer screen side 514B. An air leakage ring 532 may line an outer diameter/edge of the filter screen 514, as shown, and may seal the gap between the filter screen 514 and the mask body 501, which will be described in greater detail when referring to FIG. 6 below. The screen net 514 may function as a filter/vent for trapping any potentially harmful chemicals (e.g., smog, air pollution) from entering the user's mouth, as an example. The screen net 514 may be made from textile materials such that the screen net 514 is breathable and impermeable to water vapor, as an example, while also being able to trap harmful particles. Thus, an advantage is that the conical LED face mask may allow a user ease of breathability when the face mask is worn. The inner screen side 514A (facing toward the user's face when the mask is worn) may be sprayed with Teflon (polytetrafluoroethylene), for example, to increase the durability and waterproof quality of the screen net 514. This improved durability may increase the product lifetime of the conical LED face mask 510, since excess water vapor naturally generated by the user (via talking, exercising, for example) is prevented from infiltrating the internal mask circuitry, as another advantage.

As an example, the screen net 514 may be removeable from the rest of the mask body 501, such that the screen net 514 may be cleaned/washed and then reused, contributing to the LED face mask's overall use-life. As shown, the outer screen side 514B (facing away from the user's face when the mask is worn) may abut a second end of a central airway ("central airway," "central tunnel") 519 within the conical LED face mask 510, as an example. The outer screen side 514B may be painted/coated with a UV reflective material (e.g., silver metal) such that to increase the reflectivity within the central airway 519 while also maintaining the breathability of the filter screen 514, as an example. As an example, the central tunnel 519 may naturally become dirty overtime due to dust particles and/or pollutants in the air flowing through the central tunnel 519. As such, when the screen net 514 is removed for cleaning, the central tunnel 519 may be exposed, such that the central tunnel 519 may also be cleaned, as an example. As will be discussed in more detail below, the UV reflectivity of the outer screen side 514B may also help prevent UV-C radiation from reaching and potentially harming the user while the face mask is worn, as an advantage. It should be understood that when the conical face mask 510 is worn, the screen net 514 may be positioned over the user's nose and mouth.

As shown in FIG. 5, the mask body 501 may further comprise an outer surface 517 and an inner surface ("inner surface," "tunnel walls") 518, as an example. As an example, a volume between the outer surface 517 and the inner surface 518 may thus create a cavity 515 within the mask body 501, as shown. As an example, the tunnel walls 518 may be made of a UV transparent material, such as acrylic, such that UV light may pass into the central tunnel 519 for disinfecting. As shown, the first end 501A of the mask body 501 may be provided with a central airway tap ("central airway tap," "central filter tap," "filter tap") 534 disposed in a center of the first end 501A. As shown, the central airway tap 534 may join a first end of the central airway 519, which extends a length of the mask body 501 leading to the filter screen 514. The central airway tap 534 may be adapted to be a two-way flow port, for example, such that air can flow into and out of the LED face mask 510 through the central airway tap 534. Thus, air may be inhaled into the LED face mask 510 and exhaled out by the user through the central filter tap 534, as an example.

As shown as an example, the mask body 501 may further comprise a spiral airway tube 512 attached to the central airway tap 534, through which inhaled air may travel toward the user. As an example, a tubing length of the spiral airway tube 512 may be greater than the length of the central tunnel 519, such that the length of the central tunnel 519 is effectively extended. The extending of the central tunnel length may thus increase the disinfection effectiveness, since the inhaled air must travel a greater distance before reaching the user and is thus subject to UV light disinfection for a greater amount of time, as an example. The spiral airway tube 512 may be made of any suitable UV transparent acrylic material. The conical LED face mask 510 may be provided with both the spiral airway tube 512 and the central tunnel 519, as shown in FIG. 5, such that air inhaled by the user travels through the spiral airway tube 512 and air exhaled by the user exits through the central tunnel 519. It should be understood that, however, the spiral airway tube 512 need not be provided for inhaled air to travel toward the user. As such, both the inhaled and the exhaled air may travel through the central airway 519, as an example, resulting in a more simplified face mask structure. It should be noted that a separate outlet valve/portal may be provided in the conical mask body 501, for example, through which the exhaled air may exit the LED face mask 510 (as will be shown in FIG. 6).

As shown in FIG. 5, the conical LED face mask 510 may further comprise a plurality of UV-C LEDs 523, as an example. As shown, the plurality of LEDs 523 may be mounted on a light emission FPC sheet 513, with each LED of the plurality of LEDs 523 facing toward the central tunnel 519 and the spiral airway tube 512. Because each LED of the plurality of LEDs 523 is thus positioned parallel to the human body (when the LED face mask 510 is worn), potential direct exposure of UV-C light on the human body is greatly reduced. Thus, an advantage is that the safety of the user may be preserved during use due to the reduction of potential UV-C light exposure. As mentioned above, the plurality of LEDs 523 may be electrically connected onto the FPC sheet 513, as shown, which concentrically surrounds the central airway 519 with the arrangement of the LEDs 523 adhering to the conical shape of the LED face mask 510 in such a way that traditional printed circuit boards would not allow, as an example. As will be discussed in greater detail later, the plurality of LEDs 523 may also connect electrically to an LED driver (not shown) and vibration sensors (not shown) via the FPC sheet 513. As an example, an UV reflective layer may be provided behind the plurality of LEDs 523 and may completely line an interior of the outer surface 517, such that UV-C radiation emitted from each LED may be reflected and kept within the mask body 501, thus preventing any potential UV-C leakage from contacting the user. Additionally, the conical LED face mask 510 may also be provided with a light diffusion and scattering sheet 516 disposed in front of the plurality of LEDs 523, as shown. As described similarly previously, the light diffusion sheet 516 may scatter the UV-C light emitted by the plurality of LEDs 523, such that the UV-C light rays are more uniformly spread throughout the mask body 501 for germicidal irradiation of the air traveling in the central airway 519 and/or spiral airway tube 512, as an example.

As an example, the conical LED face mask 510 may also be provided with electrically and thermally insulating material within the mask body 501. As similarly discussed above when referring to FIGS. 2 & 3, the electrical insulation may be provided as a coating or layer lining the back surface of the UV-reflecting layer (not shown), such that the insulation is provided between the UV-reflecting layer (not shown) and the outer surface 517, as shown. As an example, the electrical insulation may prevent and minimize any potential current flow or heat transfer from reaching the inner surface 518, and potentially damaging the cone structure (e.g., melting the plastic body). As an example, the electrically insulating layer may be chosen from a wide variety of readily available materials, such as acrylic coating, plastic coating, cellular glass, etc. Additionally, because the plurality of LEDs 523 are mounted within the cavity 515 and thus away from the user, the thermal energy (i.e., heat) generated by the LEDs 523 may be focused within the mask body 501, rather than toward the user's face. Thus, an advantage is that the user may not experience uncomfortable and/or excess amounts of heat when wearing the conical LED face mask, promoting safety and comfortability.

During use, as an example, the conical LED face mask 510 may be attached onto the user's face, such that the second end 501B snugly surrounds the user's nose and mouth, and the ear straps 511 securely wrap around the user's ears, for example. The conical LED face mask 510 may be thus adapted such that, as described previously when referring to FIG. 4, the plurality of LEDs 523 emit UV-C light in or closely in synchronization with the user's breathing pattern. As the user inhales, air may be drawn into the central airway tap 534 and thus into the spinal airway tube 512. As the air is drawn to the user, and thus as the air travels within the spiral airway tube 512, the plurality of LEDs 523 emit UV-C light rays that pass through the light diffusion sheet 516 and interact with the air particles in the spiral airway tube 512, as an example. The UV irradiated air may then pass through the screen net 514, which may trap any other toxic pollutants in the air, and the filtered air may then enter the user's mouth and/or nose, as an example. The plurality of LEDs 523 may be adapted to then shut off at this time. When the user exhales, the air may be directed into the central tunnel 519 (or through a separate air channel in the mask body, as in FIG. 6) and may travel along the length of the mask body 501 toward the central filter tap 534, as an example. As the exhaled air travels through the central airway 519, the plurality of LEDs 523 again emit UV-C light rays that irradiate the exhaled air, which exits the conical LED face mask 510 through the central airway tap 534. Thus, an advantage is the prevention or minimization of the spread of infectious diseases when a user who may be infected with an infectious disease exhales, coughs, sneezes, or laughs. It should be understood that the above described process may continuously repeat as long as the user wears the conical LED face mask 510 shown in FIG. 5.

Per the example above, each LED of the plurality of LEDs 523 may be adapted to emit UV-C light at approximately 254 nm (peak absorption) for the efficient disinfection of infectious organisms in the air. As another example, and more preferably, the plurality of LEDs 523 may be adapted to emit far UV-C light at approximately 222 nm, which, as previously described when referring to FIG. 1, has been shown to be nearly harmless to human skin. However, due to the presence of the UV reflecting layer and surface coating on 514B, choosing LEDs that emit either 254 nm or 222 nm for the LED face mask 510 will work as needed. Furthermore, as described previously throughout this disclosure, pulsed current may be utilized to emit the UV-C light, which not only increases the UV light usage efficiency, but increases the current and therefore the power efficiencies. The increase in power efficiency may thus promote an increase in the rechargeable battery life since less current is flowing through the LEDs 523, as an example. Thus, an advantage is that, due to the increased battery life, the user may acquire more uses out of the conical LED face mask per each battery charge. Additionally, the improved power efficiency may also decrease the local heat generated within the conical LED face mask 510, promoting the comfortability and safety of the LED face mask shown in FIG. 5. Moreover, because less UV light is emitted overall, due to the ability to "recycle" UV light via the reflective surfaces (e.g., 514B) within the mask body 501, the chances of any harmful UV radiation contacting the user for extended periods of time are further reduced, as another advantage.

As shown in FIG. 5, the conical LED face mask 510 may be provided with the control box 540, as previously shown in FIGS. 3 & 4, for example. As shown, the conical LED face mask 510 may further comprise a connection cable 542, which may electrically connect to the LED driver (via the FPC) within the mask body 501. The connection cable 542 may be provided with an electrical connector 541, as shown, for inserting into, and making a secure electrical connection with, the control box 540. It should be understood that the control box 540 shown in FIG. 5 may functionally operate in the same manner as the control box shown in FIGS. 3 & 4 and described above. As such, the control box 540 may be provided with control circuitry (implemented on a microprocessor, for example) for controlling and timing the plurality of LEDs 523, and a rechargeable battery for powering the control box 540 and the conical LED face mask 510, as an example. It should be noted that in this exemplary embodiment of the LED face mask, the LED driver (shown by 445 in FIG. 4, for example) may be provided in the mask body 501, which is shown later in FIG. 6. As such, the control data signals (e.g., 444S in FIG. 4) may be transmitted to the LED driver (not shown) via the connection cable 542, which will be described in greater detail below.

Figure 6:
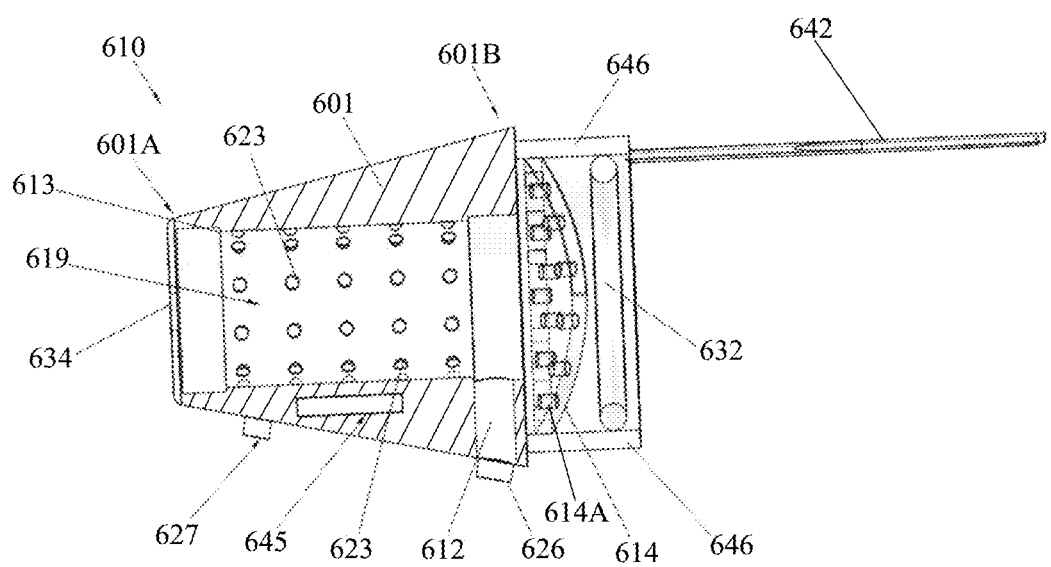
FIG. 6 illustrates a detailed left side cross-sectional view of an alternative embodiment of the conical UV-C LED disinfecting face mask shown in FIG. 5, according to an aspect.

FIG. 6 illustrates a detailed left side cross-sectional view of an alternative embodiment of the conical UV-C LED disinfecting face mask 510 shown in FIG. 5, according to an aspect. As shown in FIG. 6, some exemplary components (e.g., the UV reflecting layer, the diffusion sheet 516, and the ear straps 511) of the conical LED face mask 610 have been omitted in this view for clarity. It should be understood that aspects (e.g., thickness of the mask body 601) of the conical LED face mask 610 are not shown to scale and certain exemplary components (e.g., LEDs 623) appear larger for clarity.

As shown in FIG. 6, the conical LED face mask 610 may further comprise a power switch 627 disposed in a side of the mask body 601, as an example. As described previously when referring to FIG. 5, the conical face mask 610 may comprise the FPC 613 which provides electrical connections for the plurality of LEDs 623. As also mentioned, the FPC 613 may electrically connect to the LED driver 645, which is also disposed within the mask body 601, as shown. As described above, the conical LED face mask 610 may be provided with a connection cable 642 for establishing an electrical connection with an external control box (e.g., 540 in FIG. 5). As an example, the connection cable 642 may thus form a complete circuit between the rechargeable battery and CPU (e.g., the microprocessor) and the LED driver 645 and the plurality of LEDs 623 in the face mask 610. Thus, upon actuation of the power switch 627, electrical power may be directed from the rechargeable battery (not shown) to the LED face mask circuitry via the connection cable 642, as an example.

As previously described when referring to FIG. 5, the front end 601A of the mask body 601 may be provided with the central intake tap 634, which may provide a two-way flow point for air to enter and exit the central airway 619, as shown as an example. While the conical LED face mask 610 is depicted in FIG. 6 as having the central tunnel 619, a spiral airway tube (as in FIG. 5) may be provided in addition to or in place of the central tunnel 619. As similarly mentioned above, the spiral airway tube (not shown) may be made of acrylic having UV transparent material. As described above, air inhaled through the central airway tap 634 may travel along the central airway 619, the air being subject to UV-C light rays for disinfection as the air travels, as an example. As shown, the air may travel toward the filter screen 614 disposed at the rear end 601B of the mask body 601. As described previously above, the filter screen 614 may be removeable from the mask body 601 for cleaning and may filter out pollutants that may be present in the air, as an example. As shown in FIG. 6, the filter screen may also comprise a plurality of filter through holes 614A (similar to the air holes shown in FIG. 3, for example) through which the disinfected air may reach the user during breathing. The plurality of filter through holes 614A may also prevent pollutants and other toxins in the air from reaching the user.

As shown, the rear end 601B may also be provided with the air leakage ring 632. As an example, the air leakage ring 632 may line the edges of the rear end 601B, such that the air leakage ring 632 seals the gap between the periphery of the filter screen 614 and the rear end 601B of the mask body 601. Additionally, the air leakage ring 632 may surround the user's nose and mouth when the LED face mask 610 is worn. The air leakage ring 632 may thus further facilitate snug compression and comfortable fitting of the LED face mask 610 onto the face of the user. As an example, the air leakage ring 632 may be made of a flexible, gripping material like rubber or silicone, for example, to facilitate sealing of the LED face mask 610 onto the user's face during use. As such, the air leakage ring 632 may prevent exhaled air from leaking out the sides of the conical LED face mask 610 when worn, for example, before the exhaled air has been disinfected. Thus, an advantage is the reduction in, and prevention of, the spread of infectious diseases via a user wearing the disclosed LED face mask.

As shown in FIG. 6, the conical LED face mask 610 may further comprise a one-way outlet valve 626 disposed in a side of the mask body 601. As mentioned previously above when referring to FIG. 5, air exhaled by a user may be directed out of the LED face mask 610 via an exit point separate from the central intake valve 634. In the exemplary embodiment shown in FIG. 5, exhaled air may be directed out of the LED face mask 510 via the central airway 519 and the filter tap 534. In this alternative embodiment shown in FIG. 6, air exhaled by the user may exit via the one-way outlet valve 626, which may be adapted as a one-way airflow valve, such that air can only flow from inside the central airway 619 to outside the LED face mask 610, as an example. Per this example, the center airway tap 634 may thus also be adapted as a one-way airflow valve, such that air may only enter through the center airway tap 634. As shown, the outlet valve 626 may comprise an exit channel 629 extending between the central airway 619 and the outlet valve 626. As an example, while the user inhales and exhales, the corresponding air flows may occur naturally, such that air enters the face mask 610 via the central airway tap 634 and air exits via the one-way outlet valve 626. The exit channel 629 may also increase the exhaled air throughput for the LED face mask 610 while the user breathes, since the entry point and the exit point for respective air flows (inhale and exhale) are in different places, reducing the amount of exhaled air that naturally gets inhaled during the user's breathing cycle. Thus, an advantage is the ease of breathability of the conical LED face mask due to the natural airflows caused by the separate flow valves. As will be described in more detail below, the air inhaled and exhaled by the user may be subject to UV germicidal irradiation within the central airway 619.

As described previously when referring to FIG. 4, vibration sensors may be used to monitor, and coordinate the disinfection cycle with, the natural breathing pattern of the user. As shown in FIG. 6, the conical LED face mask 610 may be provided with a pair of vibration sensors 646 disposed at a top and a bottom ends of the rear end 601B. The vibration sensors 646 may also electrically connect to the FPC 613 and may be disposed at the rear end 601B such that to position the vibration sensors 646 as close to the user's mouth as possible when the LED face mask 610 is worn, as an example, which may allow the vibration sensors 646 to gather as accurate vibration readings as possible. Accurate vibration readings, for example, are important for establishing the breathing pattern of the user, such that the microprocessor (not shown) may instruct the LED Driver 645 to power the plurality of LEDs 623 according to the breathing pattern, as discussed when referring to FIG. 4. The accurate vibration readings, furthermore, are important for recognizing changes in the user's breathing pattern, which affect the duration of time the plurality of LEDs 623 emit UV-C light. Thus, the vibration sensors 646 continuously monitor the user's breath and continuously send the vibration data to the microprocessor (not shown). Thus, an advantage is the efficient and automatic disinfection of the air being inhaled and exhaled by the user.

Although the rechargeable battery and the microprocessor are described herein above as being separate from the conical LED face mask 610 (e.g., within the control box), it should be understood that such electrical components may alternatively be provided within the mask body 601, as an example. As an example, the rechargeable battery and the microprocessor may be selected to be sufficiently small such that to fit the rechargeable battery and the microprocessor within the mask body 601 (like the LED Driver 645). Additionally, the rechargeable battery and the microprocessor may be electrically connected to the LED Driver 645 via FPC, for example, such that to conform to the conical shape of the mask body 601. Thus, when the electrical components are adapted into the mask body 601, the power switch 627 may connect to the rechargeable battery, the rechargeable battery may connect to the microprocessor and the LED Driver 645, the microprocessor may connect to the LED Driver 645, and the LED Driver 645 may connect to the plurality of LEDs 623, all via FPC, as an example. The connection cable 642 may thus be adapted as a charging cable which can be plugged into a charging port (e.g., wall socket, USB port) for the charging of the rechargeable battery, as an example. It should be understood that the LED face masks shown in FIGS. 2, 3, & 5 may also be adapted in this way. Thus, an advantage is the ease of transportability and storability due to the compact design of the electrical components of the LED face mask.

As described previously when referring to FIG. 1, UV-C LED disinfecting systems may be provided in a number of exemplary apparatuses for personal use by a user. FIGS. 2-6 illustrated exemplary embodiments of a UV-C LED disinfecting system implemented in a face mask for a user to wear. As will be described in detail below, the UV-C LED disinfecting system of FIG. 1 may be adapted into a bag for a user to carry around in day to day life. The bag, as will be described in greater detail later, may enable the UV-C disinfecting of smaller personal items placed into the bag, as an example.

Figure 7A:
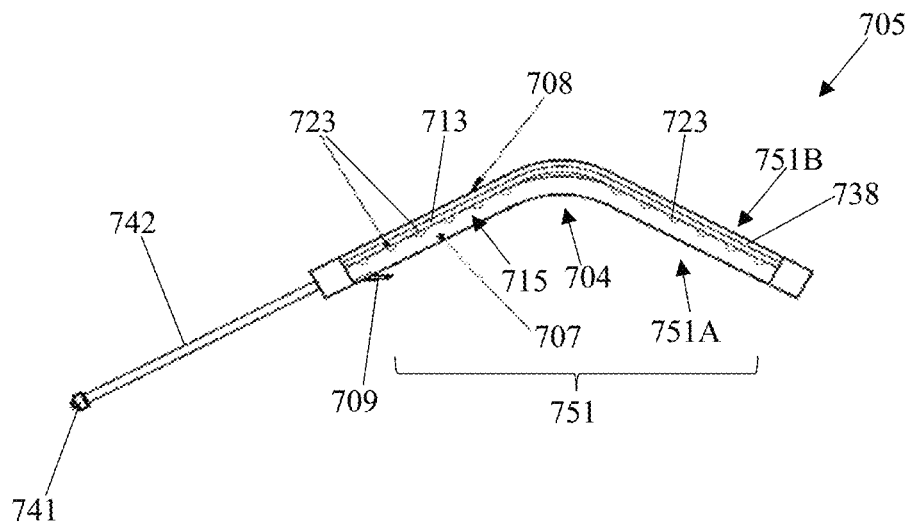
FIGS. 7A-7B illustrate a detailed top view and a detailed perspective view, respectively, of a UV-C LED disinfecting bag, according to an aspect.
Figure 7B:
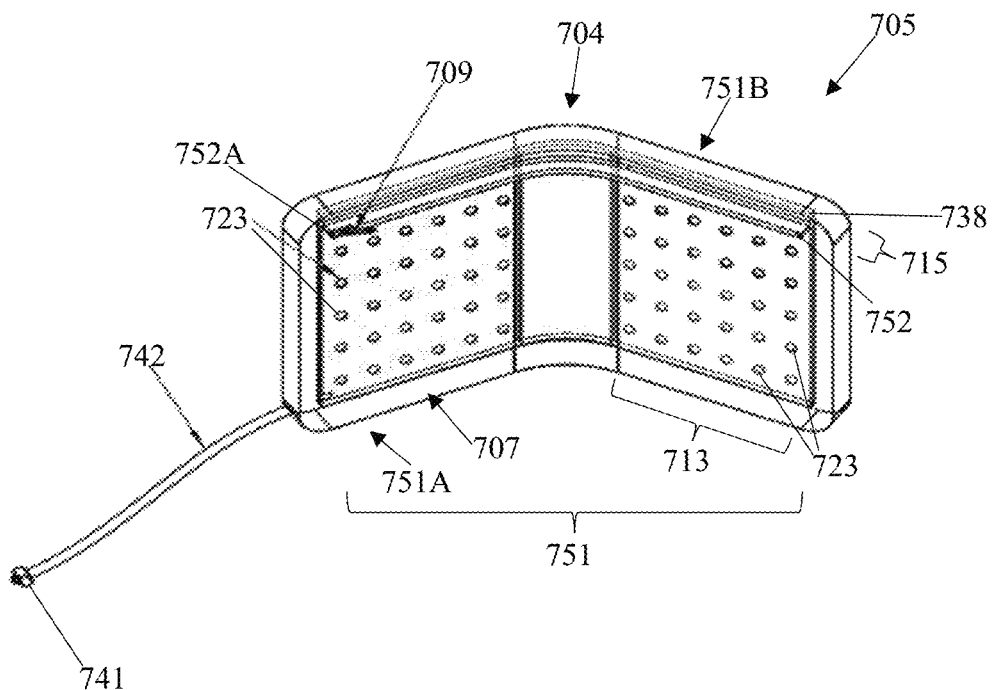

FIGS. 7A-7B illustrate a detailed top view and a detailed perspective view, respectively, of a UV-C LED disinfecting bag 705, according to an aspect. As mentioned above, the UV-C LED disinfecting bag ("UV-C LED disinfecting bag," "LED disinfecting bag," "LED sterilization bag," "LED bag") 705 may incorporate the UV-C disinfecting system of FIG. 1, such that the LED bag 705 may facilitate UV germicidal irradiation on various objects, as will be described herein below. It should be noted that the LED sterilization bag 705 may utilize a number of the same components described when referring to the LED face mask of FIGS. 2-6 above.

As shown in FIGS. 7A-7B, the LED sterilization bag 705 may comprise a bag body 751 having an interior surface 707 that forms an interior cavity ("interior cavity," "internal cavity") 715 when the LED sterilization bag 705 is opened. As shown, the bag body 751 may further comprise a front 751A and a back 751B. As shown in FIG. 7A, the LED sterilization bag 705 may comprise an exterior surface 708 lining the front 751A and the back 751B of the bag body 751. As an example, the exterior surface 708 may be made from soft and flexible materials such that the LED sterilization bag 705 can comfortably be carried by the user. Additionally, the flexible material of the exterior surface 708 may enable a suitably small object of any shape to be placed and sealed within the interior cavity 715 for disinfecting, as will be discussed later. As shown, the bag body 751 may be provided with a center fold line 704 for folding the LED sterilization bag 705 in half for ease of storage and transportation, as an example. As shown in FIGS. 7A-7B, the bag body 751 may further comprise a zipper 709 for opening and closing of the LED sterilization bag 705 along a zipper chain or teeth 752, shown in FIG. 7B, such that the interior cavity 715 can be exposed or sealed, respectively. The LED sterilization bag 705 may also be provided with carrying means (not shown), such as an arm strap or bag handles, for example, to facilitate easy transportation of the LED bag 705.

As shown, the LED sterilization bag 705 may also be provided with a plurality of UV-C LEDs 723. As shown in FIGS. 7A-7B, the plurality of LEDs 723 may be disposed within the bag body 751 and oriented to face toward the interior cavity 715, as an example. As described previously throughout this disclosure above, the plurality of LEDs 723 may be electrically connected via FPC, such that to maintain the flexibility of the LED sterilization bag 705. As shown, the plurality of LEDs 723 may be mounted onto an FPC light emitting sheet 713, which may extend a length of the bag body 751, as an example. The FPC light emitting sheet 713 may also electrically connect to a flexible cable 742, as shown, which will be described in more detail later. As shown, the LED bag 705 may further comprise a UV reflective plate or sheet 738 disposed behind the FPC light emitting sheet 713, as an example. Additionally, the LED disinfecting bag 705 may be provided with a light diffusion layer (not shown) disposed in front of the plurality of LEDs 723. As an example, the light diffusion layer may be provided as a sheet disposed between a front of the plurality of LEDs 723 and the interior surface 707. Alternatively, the light diffusion layer may be provided individually onto each LED bead of the plurality of LEDs 723, as an example.

As an example, the LED disinfecting bag 705 may also be provided with electrically and thermally insulating material within the bag body 751. As similarly discussed above when referring to the LED face mask of FIGS. 2-6, the electrical insulation may be provided as a coating or layer lining the back surface of the UV-reflecting plate 738, such that the insulation is provided between the UV-reflecting plate 738 and the exterior surface 708, as shown. As an example, the electrical insulation may prevent and minimize any potential current flow or heat transfer from reaching the back 751B of the LED sterilization bag 705, and therefore, the user. Thus, an advantage is that the user may not experience uncomfortable and/or excess amounts of heat when holding/wearing the LED sterilization bag, promoting safety and comfortability. As an example, the electrically insulating layer may be chosen from a wide variety of readily available materials, such as acrylic coating, plastic coating, cellular glass, etc.

As described throughout this disclosure, the plurality of LEDs 723 may be adapted to emit UV-C light to facilitate UV germicidal irradiation on a target object (e.g., air particles). The LED bag 705 shown in FIGS. 7A-7B may be adapted for sterilizing a plurality of handheld items, such as cellphones, car keys, watches, headphones, pens, and even mail, essentially any object able to fit within the interior cavity 715 of the LED sanitizing bag 705. During use, as an example, the user may unzip the LED sanitizing bag 705 via the zipper 709, such that the interior cavity 715 is exposed. Then, the user may place a handheld object(s) into the interior cavity 715 and zip the LED bag 705 closed, such that the interior cavity 715 containing the object(s) is sealed. The plurality of LEDs 723 may be thus adapted to emit UV-C light directed toward the interior cavity 715 and onto the object(s) sealed inside. As mentioned above, the bag body 751 may comprise the front 751A and back 751B surfaces, as shown in FIGS. 7A-7B. While the LED sterilization bag 705 is in disinfecting mode (i.e., emitting UV light), the bag body 751 may be folded along the center fold line 704, or may be placed onto a hard surface or worn by the user, such that the back 751B rests on the hard surface or brushes against the user's body, respectively. Thus, the UV-C light emitted by the plurality of LEDs may be directed outwardly and/or away from the user's body, as an example. Thus, an advantage is that the safety and wellbeing of the user may be maintained due to the reduction in potential direct exposure to UV-C light rays.

Per the example above, as the plurality of LEDs 723 emit UV-C light, the UV-C light rays pass through the light diffusion layer (not shown), which causes the UV-C light to scatter and spread more uniformly throughout the interior cavity 715. Simultaneously, the UV reflecting sheet 738 positioned behind the plurality of LEDs 723 may prevent any UV-C light from leaking out of the bag body 751, and thus provides an additional safety feature for the user, as an advantage. The UV reflecting sheet 738 may also cause the UV light to bounce back toward the internal cavity 715, facilitating improved UV light usage efficiency, since the UV light is essentially "recycled" within the bag body 751. Furthermore, the UV light rays reflected by the UV reflecting sheet 738 may contribute to the UV sterilization of the object(s) contained inside the interior cavity 715. Thus, an advantage is the efficient and safe UV sterilization of various objects placed within the LED sterilization bag. As will be described in more detail herein below, the plurality of UV-C LEDs 723 may be adapted to turn off automatically, at which point the user may unzip the LED sterilization bag 705 and safely retrieve the disinfected object(s), per the example.

As an example, the LED sterilization bag 705 may be provided with a separate portable case (not shown). As mentioned above, the LED sterilization bag 705 may be provided with the flexible cable 742, as shown. The flexible cable 742 may comprise an electrical connector 741, as shown in FIGS. 7A-7B, which may be inserted and connected to the portable case or module (not shown). As an example, the LED sterilization bag 705 may be placed inside the portable case (not shown) when not in use, such that the LED sterilization bag 705 may be safely transported and stored for longer periods of time in between uses. As described in reference to the LED face mask shown in FIGS. 2-6 above, an LED Driver and control circuitry may be provided for driving the plurality of LEDs 723. As an example, let the control circuitry be implemented on a CPU (e.g., a microprocessor), and let the CPU electrically connect to the LED Driver (as in FIG. 4, for example). As similarly described in this disclosure above, the microprocessor (not shown) and the LED Driver (not shown) may draw power from a rechargeable battery (not shown). The microprocessor, LED Driver, and rechargeable battery may thus be implemented into the portable case described above. The LED Driver may thus establish an electrical connection with the FPC light emission sheet 713 having the plurality of LEDs 723 when the flexible cable 742 is plugged into the portable case or module, as an example. Finally, a power switch/button (not shown) may be provided on the portable case or on the bag body 751, for example, for directing power to the microprocessor and "turning on" of the LED sterilization bag 705.

It should be understood that the rechargeable battery may be provided with a charging means (via an external charging cable, for example) for charging of the rechargeable battery. It should be noted that the rechargeable battery, the microprocessor, and the LED Driver may be provided within the bag body 751, rather than separately in the portable case. As such, the rechargeable battery (connected to the power switch), the microprocessor, and the LED Driver may be electrically connected on the FPC sheet 713, with the appropriate electrical connections made between each component (e.g., wiring the microprocessor to the LED Driver). Thus, the rechargeable battery, the microprocessor, and the LED Driver may be chosen and/or adapted to be sufficiently small in size so as to fit within the bag body 751. It would thus be preferable to also supply electrical insulation and a UV-reflective surface over these electrical components such that to minimize additional heat generated by the rechargeable battery, the microprocessor, and the LED Driver, as an example.

As mentioned herein above, the plurality of LEDs 723 may be adapted to be automatically turned on and off for disinfecting of an object(s) that is placed within the bag body 751. As an example, the microprocessor may be programmed with a timer function to set an optimal UV radiation time for disinfecting the object(s) contained in the interior cavity 715. For example, during the disinfecting cycle, the microprocessor may be programmed to emit UV-C light from the plurality of LEDs 723 for 60 seconds and then turn off the plurality of LEDs 723, completing the disinfecting cycle. Alternatively, for example, the microprocessor may emit UV-C light in pulses, such that, for example, the plurality of LEDs are turned on for 0.05 seconds and then are turned off for 0.05 second, then on for 0.05 seconds, and so on, for a predetermined number of disinfecting cycles. As mentioned previously when referring to FIG. 1, some (or all) of the LED modules 723 may be provided with fluorescent materials (e.g., powder) for optical wavelength shifting. As an example, the fluorescent powder causes a fluorescent flaring effect to help maintain the stimulated UV-C radiation of each LED for a short period of time before decaying to zero. Essentially, the fluorescent powder may compensate for the times during the UV-C emission cycle that the current supply is zero (i.e., the LEDs are off). Thus, the user need not manually control the UV light emission cycles, increasing the ease of usability of the LED sterilization bag, as an advantage.

As similarly described herein above when referring to the LED face mask apparatus, the microprocessor may send control signals to the LED Driver, which then turns on and off the plurality of LEDs 723 according to the control signals, as an example. As discussed, the LED Driver may provide pulsed current outputs (as shown in FIG. 4, for example) to the plurality of LEDs 723 to turn on and off the LEDs, as an example. The pulsed current outputs, as previously described, may use less electrical power, leading to increased battery life and improved power efficiency. Thus, an advantage is that, due to the increased battery life, the user may acquire more uses out of the LED sterilization bag on each battery charge. The increase in power efficiency may thus also reduce local heat accumulated within the LED sterilization bag 705 since less current is flowing through the LEDs 723, which may increase user comfort and safety during use, as another advantage. The increase in power and current efficiencies may therefore also increase the use-life of the LED sterilization bag 705, since burnout of the rechargeable battery and/or the plurality of LEDs 723 will be prolonged, as an example.

Finally, the LED sterilization bag 705 may be provided with a safety switch (not shown) built into the bag body 751. As an example, the safety switch may be a pair of sensors (e.g., magnetic sensors) placed near and/or along the zipper chain 752, which may detect when the LED sterilization bag 705 is open (i.e., unzipped) or closed (i.e., zipped). As another example, the safety switch may be a light sensor (e.g., a photoresistor) used to measure light within the bag cavity 715, detecting when the LED sterilization bag 705 is open (i.e., having light within the cavity 715) or closed (i.e., having complete darkness within the cavity 715). The safety switch (not shown) may also be electrically connected to the FPC sheet 713, such that the safety switch may send input data to the microprocessor via the FPC sheet 713, for example. The safety switch (implemented as a magnetic switch) may be placed at a first end 752A of the zipper chain 752, such that the input data sent to the microprocessor may indicate whether the LED sterilization bag 705 is completely zipped closed, as an example. The safety switch (implemented as a light sensor) may alternatively be placed within the bag body 751 such that to detect any light within the interior cavity 715, as an example. The microprocessor may not initialize the disinfecting cycle (e.g., activate the plurality of LEDs 723) unless the bag body 751 is completely closed (i.e., the internal cavity 715 is sealed). The safety switch may thus ensure that premature UV light emission does not occur, which could cause dangerous UV light exposure for the user or other humans surrounding the user. As another example, while the plurality of LEDs 723 are emitting UV-C light, should the zipper 709 accidentally be caused to open/unzip, the safety switch may alert the microprocessor, which will then cause a deactivation of the plurality of LEDs 723. The safety switch may thus ensure that, during operation, the UV-C light is maintained solely within the interior cavity 715 of the bag body 751, thus also promoting user safety. Thus, an advantage is the prevention of potentially dangerous UV-C radiation exposure due to the safe and automatic operation of the UV-C LEDs of the LED sterilization bag.

It should be understood that the LED sterilization bag 705 disclosed above may be adapted as a bag having other shapes and configurations. As an example, the LED sterilization bag 705 may be adapted as an LED sterilization purse, backpack, suitcase, handbag, wallet, or tote bag, as examples. Additionally, the LED sterilization bag 705 may be adapted to be compartmentalized, such that multiple interior cavities (715) are provided throughout the bag body (751) for UV disinfecting of objects of different sizes at the same time. It should also be understood that other sealing means may be provided in place of the zipper (709) and zipper chain (752). As an example, the LED sterilization bag 705 could be provided with Velcro® straps, adhesive tape, buttons/snap fasteners, or magnets, as examples, for sealing the body of the bag closed for safe UV light sterilization.

As mentioned herein above, the LED sterilization bag 705 may be adapted to receive various objects for UV disinfecting of the various objects within the bag body 751. Various objects in a user's day to day life may contain potentially infectious microorganisms living on the objects' surfaces. These objects may be in the user's home or out in public, such as in grocery stores, restaurants, and shopping centers, for example. So many objects come into contact with other people who may or may not be taking the necessary precautions in their daily lives to prevent the spread of infectious diseases. The LED sterilization bag 705 may thus provide the user with a safe, efficient, and automatic apparatus for disinfecting these various objects potentially containing infectious viruses, bacteria, and other pathogens. Thus, an advantage is that the UV-C LED disinfecting apparatuses disclosed herein above may not only provide the user with an effective UV germicidal irradiation instrument but may also provide the user with peace of mind.

It should be understood that the UV-C LED disinfecting system disclosed herein may be adapted into a plurality of other apparatuses not shown or discussed throughout this disclosure. Implementation of the UV-C LED disinfecting system into household and retail items for object disinfection by users is well within the scope and bounds of the presently described embodiments. It should also be understood that the central processing unit may be chosen from any suitable single chip CPU variety other than microprocessors.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

Additionally, as used in this application, the phrase "UV-C LED" refers to an LED or LEDs adapted to emit light along the UV-C spectrum, particularly 200-280 nm. It should be understood that the terms "disinfecting," "sterilizing," "sanitizing," and "irradiating" are used in this application interchangeably. In the same light, the terms "disinfection," "sterilization," "sanitization," and "irradiation" are also used in this application interchangeably. The terms and phrases "light," "light rays," "rays," "light radiation," and "radiation" are used in this application interchangeably as well.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

Claim limitations should be construed as means-plus-function limitations only if the claim recites the term "means" in association with a recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples. Hence, the scope of the invention is defined by the accompanying claims and their equivalents. Further, each and every claim is incorporated as further disclosure into the specification.

What is claimed is:

1. An ultraviolet (UV) germicidal irradiation system for disinfecting of air, the UV germicidal irradiation system comprising:
    a light emitting diode (LED) disinfecting face mask adapted to be worn on a user's face, the LED disinfecting face mask comprising:
        a conical mask body, the conical mask body having:
            an exterior surface;
            a front end and a back end; and
            a central tunnel disposed centrally within and extending a length of the conical mask body;
        the back end being adapted to contact the user's face when the LED disinfecting face mask is worn;
        a flexible printed circuitry (FPC) sheet disposed within the conical mask body such that to concentrically surround the central tunnel, the FPC sheet having a plurality of LEDs adapted to emit UV light, each LED of the plurality of LEDs being oriented to face inwardly toward the central tunnel;
        at least one vibration sensor electrically connected to the FPC sheet, the at least one vibration sensor being adapted to detect vibrations in the conical mask body caused by the user's breathing when the LED disinfecting face mask is worn;

an UV-reflective layer disposed behind the FPC sheet along an interior of the exterior surface, the UV-reflective layer being adapted to reflect the UV light emitted by the plurality of LEDs, such that the emitted UV light is fully contained within the conical mask body and can thus disinfect air flowing through the central tunnel when the LED disinfecting face mask is worn;

a center airway tap disposed centrally in the front end, the center airway tap joining a first end of the central tunnel;

a removable filter screen disposed centrally in the back end, the removable filter screen joining a second end of the central tunnel; and a control module adapted to be electrically connected to the plurality of LEDs, the control module comprising:
a central processing unit (CPU);
an LED driver adapted to activate and deactivate the plurality of LEDs; and
a power source adapted to supply electrical power to the CPU and the LED driver;
the CPU being in electrical communication with the at least one vibration sensor and the LED driver;

the LED disinfecting face mask and the control module being thus adapted such that while the LED disinfecting face mask is worn on the user's face, and while the user breathes, the plurality of LEDs emit the UV light, such that the emitted UV light disinfects the air flowing through the central tunnel.

2. The UV germicidal irradiation system of claim 1, wherein the LED disinfecting face mask further comprises:

a light diffusion layer disposed within the conical mask body in front of the FPC sheet, the light diffusion layer being adapted to scatter the emitted UV light throughout the central tunnel; and a pair of stretchable straps attached at opposite sides of the back end.

3. The UV germicidal irradiation system of claim 1, wherein the LED disinfecting face mask further comprises:

an air leakage ring disposed around a periphery of the removable filter screen, the air leakage ring forming a seal between the periphery and the back end; and a spiral airway tube connected to the center airway tap, the spiral airway tube spiraling around the central tunnel and concluding at the back end, such that air being inhaled by the user flows through the spiral airway tube.

4. The UV germicidal irradiation system of claim 1, wherein the LED disinfecting face mask further comprises:

an outlet valve disposed in the exterior surface toward the back end; and an exit channel extending between the outlet valve and the central tunnel, such that air being exhaled by the user flows out of the outlet valve through the exit channel.

5. The UV germicidal irradiation system of claim 1, wherein the plurality of LEDs are adapted to emit UV light having wavelengths between 200-280 nm.

6. The UV germicidal irradiation system of claim 1, wherein the CPU is a microprocessor and the power source is a battery.

7. The UV germicidal irradiation system of claim 6, wherein the control module is integral to the conical mask body.

* * * * *